(12) United States Patent
Marcantonio et al.

(10) Patent No.: US 12,059,426 B2
(45) Date of Patent: Aug. 13, 2024

(54) PHARMACEUTICAL COMPOSITIONS COMPRISING A RYANODINE RECEPTOR MODULATOR AND USES THEREOF

(71) Applicant: ARMGO Pharma, Inc., Ardsley, NY (US)

(72) Inventors: Eugene E. Marcantonio, Tenafly, NJ (US); Mette Uhre Anby, Frederiksberg (DK); Jérôme Binet, Saint Denis en Val (FR)

(73) Assignee: ARMGO Pharma, Inc., Ardsley, NY (US)

( * ) Notice: Subject to any disclaimer, the term of this patent is extended or adjusted under 35 U.S.C. 154(b) by 0 days.

(21) Appl. No.: 18/221,784

(22) Filed: Jul. 13, 2023

(65) Prior Publication Data

US 2023/0364107 A1  Nov. 16, 2023

Related U.S. Application Data

(62) Division of application No. 17/748,886, filed on May 19, 2022, now Pat. No. 11,717,526.

(60) Provisional application No. 63/191,142, filed on May 20, 2021.

(51) Int. Cl.
A61K 31/554 (2006.01)
A61K 9/28 (2006.01)
A61P 21/00 (2006.01)

(52) U.S. Cl.
CPC ......... *A61K 31/554* (2013.01); *A61K 9/2866* (2013.01); *A61K 9/2886* (2013.01); *A61P 21/00* (2018.01)

(58) Field of Classification Search
CPC ...... A61K 31/554; A61K 47/12; A61K 47/14; A61K 47/20; A61K 9/0053; A61K 9/2866; A61K 9/2886; A61P 21/00
See application file for complete search history.

(56) References Cited

FOREIGN PATENT DOCUMENTS

PT  2163248 E  * 12/2012  ........... A61K 31/554

OTHER PUBLICATIONS

PT2163248E translation (Year: 2012).*

* cited by examiner

*Primary Examiner* — Audrea B Coniglio
(74) *Attorney, Agent, or Firm* — Wilson Sonsini Goodrich & Rosati

(57) ABSTRACT

The present disclosure provides a modified-release pharmaceutical composition comprising 4-[(7-methoxy-2,3-dihydro-1,4-benzothiazepin-4(5H)yl)methyl]benzoic acid hemifumarate, and a pharmaceutically-acceptable excipient. The present disclosure methods of treating conditions associated with RyRs, including, for example, cardiac disorder or disease, a musculoskeletal disorder or disease, cancer associated muscle weakness, malignant hyperthermia, and diabetes.

12 Claims, 9 Drawing Sheets

PHARMACEUTICAL COMPOSITIONS COMPRISING A RYANODINE RECEPTOR MODULATOR AND USES THEREOF

CROSS REFERENCE

This application is a divisional of U.S. application Ser. No. 17/748,886, filed May 19, 2022, which claims the benefit of U.S. Provisional Application No. 63/191,142, filed May 20, 2021, each of which is incorporated by reference herein in its entirety.

STATEMENT REGARDING GOVERNMENT SUPPORT

This invention was created in the performance of a Cooperative Research and Development Agreement with the National Institutes of Health, an Agency of the Department of Health and Human Services. The Government of the United States has certain rights in this invention.

BACKGROUND

The sarcoplasmic reticulum (SR) is a structure in cells that functions, among other things, as a specialized intracellular calcium ($Ca^{2+}$) store. Ryanodine receptors (RyRs) are channels in the SR that open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability of RyRs refers to the likelihood that a RyR is open at any given moment, and therefore capable of releasing $Ca^{2+}$ into the cytoplasm from the SR. Three RyR isoforms are known. RyR1 is the predominant isoform expressed in mammalian skeletal muscle, RyR2 is predominantly found in cardiac muscle, whereas RyR3 expression is low in skeletal muscle.

$Ca^{2+}$ release from the SR is modulated by several RyR binding proteins. Calstabin1 (FKBP12) and Calstabin2 (FKBP12.6) stabilize the closed state of the RyR1 and RyR2, respectively. Mutations in RYR1 or RYR2 are characterized by reduced binding of Calstabin1 or Calstabin2, respectively, and inappropriate channel opening not related to contraction signals. This channel opening is further exacerbated by post-translational modifications such as PKA-phosphorylation, oxidation, or nitrosylation of the RyR channel. The resulting dissociation of Calstabin can lead to leaky channels, which exhibit a pathologic increase in the open probability under resting conditions. The SR $Ca^{2+}$ leak leads to a reduction in SR $Ca^{2+}$ content, with less $Ca^{2+}$ available for release and consequently weaker muscle contractions.

SUMMARY

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 2 to about 6 hours after administration.

In some embodiments, the present disclosure provides a method of treating a condition, comprising administering to a subject in need thereof a therapeutically-effective amount of a pharmaceutical composition, the pharmaceutical composition comprising in a unit dosage form 4-[(7-methoxy-2,3-dihydro-1,4-benzothiazepin-4(5H)yl)methyl]benzoic acid or the pharmaceutically-acceptable salt thereof, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

In some embodiments, the present disclosure provides a tablet comprising a core, a sub-coating layer substantially covering the core, and a coating layer substantially covering the sub-coating layer, wherein
- the core comprises 4-[(7-methoxy-2,3-dihydro-1,4-benzothiazepin-4(5H)yl)methyl]benzoic acid hemifumarate, mannitol, microcrystalline cellulose, croscarmellose sodium, magnesium stearate, maltodextrin, colloidal anhydrous silica, and sodium stearyl fumarate;
- the sub-coating layer comprises hypromellose, microcrystalline cellulose and stearic acid; and
- the coating layer comprises hypromellose acetate succinate, triethyl citrate, sodium lauryl sulfate and talc.

In some embodiments, the present disclosure provides a tablet comprising a core, a sub-coating layer substantially covering the core, and a coating layer substantially covering the sub-coating layer, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 2 to about 6 hours after administration. In some embodiments, a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 3 to about 4 hours after administration.

DETAILED DESCRIPTION

Figure 1:
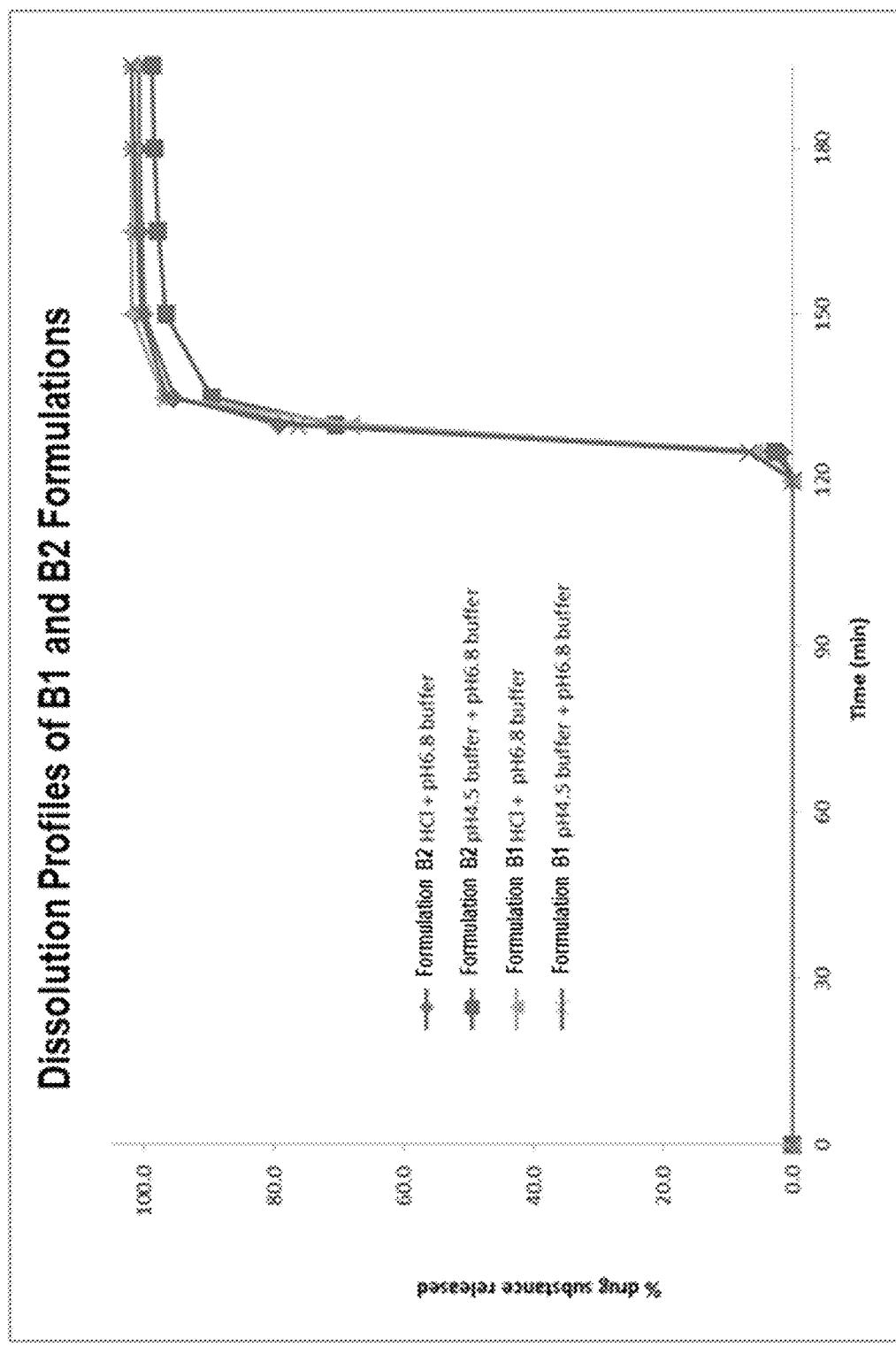
FIG. 1: In vitro dissolution time profiles of gastro-resistant tablets of Example 2 (Formulation B1) and Example 3 (Formulation B2) in pH 1-2 (0.1N HCl) or pH 4.5 buffer, followed by pH 6.8 buffer.

The present disclosure provides a modified-release pharmaceutical composition comprising 4-[(7-methoxy-2,3-dihydro-1,4-benzothiazepin-4(5H)yl)methyl]benzoic acid or a pharmaceutically-acceptable salt thereof, e.g., a hemifumarate salt, and a pharmaceutically-acceptable excipient. The present disclosure methods of treating conditions associated with RyRs, including, for example, cardiac disorder or disease, a musculoskeletal disorder or disease, cancer associated muscle weakness, malignant hyperthermia, and diabetes.

The compound 4-[(7-methoxy-2,3-dihydro-1,4-benzothiazepin-4(5H)yl)methyl]benzoic acid has the following chemical structure:

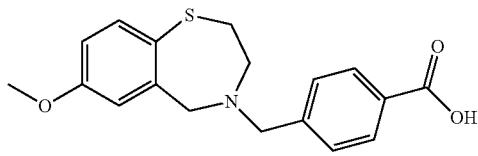

In some embodiments, 4-[(7-methoxy-2,3-dihydro-1,4-benzothiazepin-4(5H)yl)methyl]benzoic acid is provided in the form of a salt with a pharmaceutically-acceptable acid or base. Non-limiting examples of salts include sodium, potassium, magnesium, hemifumarate, hydrochloride and hydrobromide salts. In one embodiment, the salt is a sodium salt. In another embodiment, the salt is a hemifumarate salt.

When present as a hemifumarate salt, the compound is herein designated Compound (I). Compound (I) has an empirical formula possessing the following structure or an ionized form thereof:

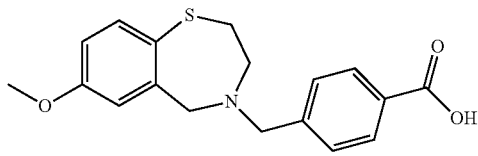 [SMILES: COc1ccc2c(c1)CN(Cc1ccc(C(=O)O)cc1)CCS2]

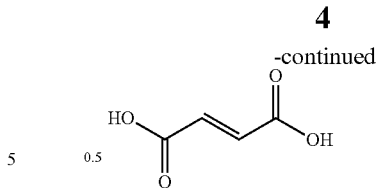

For example, a compound of formula (I) may be in ionized form, comprising two ionized molecules of 4-[(7-methoxy-2,3-dihydro-1,4-benzothiazepin-4(5H)yl)methyl]benzoic acid.

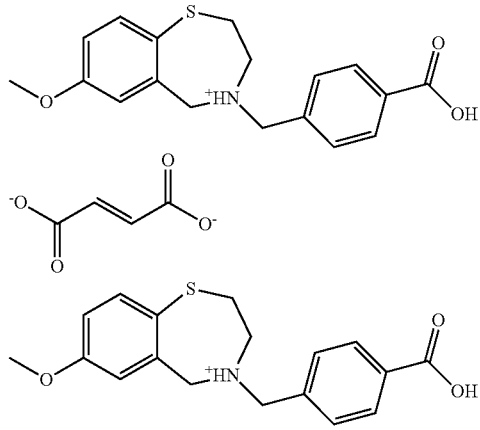

Pharmaceutical Compositions

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

In some embodiments, the present disclosure provides a pharmaceutical composition comprising in a unit dosage form 4-[(7-methoxy-2,3-dihydro-1,4-benzothiazepin-4(5H)yl)methyl]benzoic acid hemifumarate, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

In some embodiments, the pharmaceutical composition provides modified-release of the active ingredient, i.e., 4-[(7-methoxy-2,3-dihydro-1,4-benzothiazepin-4(5H)yl)methyl]benzoic acid or a pharmaceutically-acceptable salt thereof. In some embodiments, the pharmaceutical composition provides prolonged release of the active ingredient, for example, 4-[(7-methoxy-2,3-dihydro-1,4-benzothiazepin-4(5H)yl)methyl]benzoic acid or the pharmaceutically-acceptable salt thereof. In some embodiments, the pharmaceutical composition provides controlled release of the active ingredient, for example, 4-[(7-methoxy-2,3-dihydro-1,4-benzothiazepin-4(5H)yl)methyl]benzoic acid or a pharmaceutically-acceptable salt thereof. In some embodiments, the pharmaceutical composition provides extended release of the active ingredient, for example, 4-[(7-methoxy-2,3-dihydro-1,4-benzothiazepin-4(5H)yl)methyl]benzoic acid or a pharmaceutically-acceptable salt thereof. In some embodiments, the pharmaceutical composition provides sustained release of the active ingredient, for example, 4-[(7-methoxy-2,3-dihydro-1,4-benzothiazepin-4(5H)yl)methyl] benzoic acid or a pharmaceutically-acceptable salt thereof. In some embodiments, the pharmaceutical composition provides delayed release of the active ingredient, for example, 4-[(7-methoxy-2,3-dihydro-1,4-benzothiazepin-4(5H)yl) methyl]benzoic acid or a pharmaceutically-acceptable salt thereof.

In some embodiments, the pharmaceutical composition provides modified-release of the active ingredient, for example, 4-[(7-methoxy-2,3-dihydro-1,4-benzothiazepin-4(5H)yl)methyl]benzoic acid hemifumarate. In some embodiments, the pharmaceutical composition provides prolonged release of the active ingredient, for example, 4-[(7-methoxy-2,3-dihydro-1,4-benzothiazepin-4(5H)yl)methyl]benzoic acid hemifumarate. In some embodiments, the pharmaceutical composition provides controlled release of the active ingredient, for example, 4-[(7-methoxy-2,3-dihydro-1,4-benzothiazepin-4(5H)yl)methyl]benzoic acid hemifumarate. In some embodiments, the pharmaceutical composition provides extended release of the active ingredient, for example, 4-[(7-methoxy-2,3-dihydro-1,4-benzothiazepin-4(5H)yl) methyl]benzoic acid hemifumarate. In some embodiments, the pharmaceutical composition provides sustained release of the active ingredient, for example, 4-[(7-methoxy-2,3-dihydro-1,4-benzothiazepin-4(5H)yl)methyl]benzoic acid hemifumarate. In some embodiments, the pharmaceutical composition provides delayed release of the active ingredient, for example, 4-[(7-methoxy-2,3-dihydro-1,4-benzothiazepin-4(5H)yl)methyl]benzoic acid hemifumarate.

Gastro-Resistant Formulations

In some embodiments, a modified-release formulation is a gastro-resistant formulation. In some embodiments, a modified-release formulation is a gastro-resistant formulation in unit dosage form. In some embodiments, a modified-release formulation is a gastro-resistant formulation in a unit solid dosage form.

In some embodiments, a delayed-release formulation is a gastro-resistant formulation. In some embodiments, a delayed-release formulation is a gastro-resistant formulation in unit dosage form. In some embodiments, a delayed-release formulation is a gastro-resistant formulation in a unit solid dosage form. In some embodiments, a gastro-resistant formulation is a gastro-resistant tablet.

Gastro-resistant tablets are delayed-release tablets that can resist acidic gastric fluid and release their active substance(s) in the intestinal fluid. Gastro-resistant tablets can be prepared from granules or particles already covered with a gastro-resistant coating or alternatively by covering tablets with a gastro-resistant coating (e.g., enteric-coated tablets). The pH range of fluids in various segments of the gastrointestinal tract provide environmental stimuli for responsive drug release.

In some embodiments, enteric-coated gastro-resistant tablets are composed of three layers: (1) a drug-containing core tablet (immediate release function); (2) a subcoat layer substantially covering the core, which subcoat layer can include a swellable, hydrophobic polymer layer (e.g., hydroxypropyl cellulose or hypromellose (hydroxypropylmethyl cellulose) (time release function)); and (3) an enteric coating layer comprising an enteric polymer, the enteric coating layer substantially covering the subcoat layer (acid resistance function). The tablet does not substantially release the drug in the stomach due to the acid resistance of the outer enteric coating layer. The enteric coating layer rapidly dissolves after gastric emptying and the intestinal fluid begins to erode the subcoat polymer layer. Rapid drug release occurs after the erosion front reaches the core tablet after gastric emptying. The time needed for the core tablet to become accessible by dissolution of the eroding layers is the lag phase, the duration of which can be controlled either by the mass or composition of the polymer in the subcoat layer.

In some embodiments, a gastro-resistant formulation is a delayed-release formulation due to, e.g., sensitivity to pH resulting from an enteric coating, and a modified-release formulation due to, e.g., the presence of a polymer in the subcoat layer. In some embodiments, a formulation is characterized by a delayed-release profile such that all or substantially all of the formulation transits the stomach and is released in the small intestine. In addition, due to the presence of a polymer in the subcoating layer, slow erosion of the formulation (lag phase) can result in prolonged-release of the active ingredient relative to an immediate release formulation. In some embodiments, a gastro-resistant formulation has a release profile that is a combination of delayed-release profile due, e.g., to presence of an enteric coating, and prolonged-release profile due, e.g., to presence of a polymer, for example due to the presence of a polymer in a subcoat layer.

In some embodiments, the gastro-resistant formulation is resistant to disintegration in gastric fluid. For example, in some embodiments, less than about 10%, less than about 9%, less than about 8%, less than about 7%, less than about 6%, less than about 5%, less than about 4%, less than about 3%, less than about 2%, or less than about 1% of the active ingredient is released from the formulation in gastric fluid or at a pH mimicking that of gastric fluid. A pH of gastric fluid varies with the presence or absence of food, and typically ranges from about 1.5 to about 3.5. In some embodiments, the gastro-resistant formulation does not substantially disintegrate for at least about 15 minutes after exposure to gastric fluid. For example, the gastro-resistant formulation does not substantially disintegrate for at least about 30 minutes or at least about 45 minutes or at least about 60 minutes or at least about 75 minutes or at least about 90 minutes or at least about 120 minutes or at least about 180 minutes or even longer after exposure to gastric fluid. In some embodiments, the gastro-resistant formulation is resistant to disintegration in gastric fluid in the absence of food. In some embodiments, the gastro-resistant formulation is resistant to disintegration in gastric fluid in the presence of food.

In some embodiments, the gastro-resistant formulation (e.g., a gastro-resistant tablet) does not substantially disintegrate at a pH at or below 5.5. For example, the gastro-resistant formulation (e.g., gastro-resistant tablet) releases less than about 10% of an active ingredient at a pH at or below 5.5. For example, the gastro-resistant formulation (e.g., gastro-resistant tablet) releases less than about 9%, less than about 8%, less than about 7%, less than about 6%, less than about 5%, less than about 4%, less than about 3%, less than about 2%, or less than about 1% of an active ingredient at a pH at or below about 5.5.

In some embodiments, the gastro-resistant formulation does not substantially disintegrate after exposure to a pH at or below about 5.5, e.g., a pH at or below about 4.5, about 4.0, about 3.5, about 3.0, about 2.5, about 2.0, or lower. In some embodiments, the gastro-resistant formulation does not substantially disintegrate for at least about 15 minutes after exposure to a pH at or below about 5.5. For example, the gastro-resistant formulation does not substantially disintegrate for at least about 30 minutes or at least about 45 minutes or at least about 60 minutes or at least about 75 minutes or at least about 90 minutes or at least about 120 minutes or at least about 180 minutes or even longer after exposure to a at or below pH below about 5.5.

In some embodiments, the gastro-resistant formulation (e.g., gastro-resistant tablet) substantially disintegrates at neutral pH (pH=7), or a pH that is close to neutral, e.g., a pH 6.8, or higher. In some embodiments, delayed-release formulations release at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99% at a pH about 6.8 or higher. Such release can occur rapidly, e.g., within 30 minutes, or 40 minutes, or 50 minutes, or 60 minutes, or 120 minutes, or 180 minutes after the enteric layer and/or the subcoat layer are eroded and the drug-containing core is exposed.

In some embodiments, the gastro-resistant formulation (e.g., tablet) comprises an enteric coating layer. Enteric coated tablets are solid, oral unit dosage forms that are designed to pass through the stomach and release the drug in the small intestine. In some embodiments, enteric coatings prevent release of the active ingredient before the tablet reaches the small intestine. Once the formulation reaches the small intestine, the enteric coating dissolves and the active ingredient is released. Release of the active ingredient can be according to an immediate release profile, e.g., at least about 70%, at least about 75%, at least about 80%, at least about 85%, at least about 90%, at least about 95%, at least about 95%, at least about 96%, at least about 97%, at least about 98%, or at least about 99% of the active ingredient is released within 1 hour of reaching the small intestine.

In some embodiments, disintegration is determined by measuring dissolution of a gastro-resistant formulation in a medium having a pH of less than 5.5, e.g., a pH between about 1.0 and about 2.0, or a pH between about 4.0 and 5.0, e.g., a pH of about 4.5. In some embodiments, disintegration is determined by measuring dissolution of a gastro-resistant formulation in a medium having a pH of about 6.5 to about 7.0, e.g, a pH of about 6.8.

In some embodiments, the medium having a pH below 5.5 is a HCl solution having a pH of about 1.2. In some embodiments, the medium having a pH below 5.5 is a 0.1N HCl solution having a pH of about 1.2. In some embodiments, the medium having a pH of 6.8 is a phosphate buffer.

In some embodiments, an enteric coating layer rapidly dissolves after gastric emptying and the intestinal fluid begins to erode the subcoat polymer layer. Rapid drug release occurs after the erosion front reaches the core tablet after gastric emptying. The time needed for the core tablet to become accessible by dissolution of the eroding layers is designated the "lag phase". In some embodiments, duration of the lag phase may be controlled by varying the mass of the polymer in the subcoat layer. In some embodiments, duration of the lag phase is controlled by varying the nature of the polymer in the subcoat layer. In some embodiments, the duration of the lag phase is controlled by varying the mass and composition of the polymer in the subcoat layer. In some embodiments, the polymer is hydroxypropylcellulose. In some embodiments, the polymer is hypromellose (hydroxypropylmethyl cellulose).

In some embodiments, a gastro-resistant pharmaceutical composition of the present disclosure is administered to the subject in a fed state (e.g., during a meal or within at most about 1 hour, about 2 hours, about 3 hours, about 4 hours, about 5 hours, about 6 hours, or about 7 hours after a meal).

In some embodiments, a gastro-resistant pharmaceutical composition of the present disclosure is administered to the subject in a fasted state (e.g., at least 8 about hours, at least about 9 hours, at least about 10 hours, at least about 11 hours, or at least about 12 hours after a meal, or longer). In some embodiments, a meal is a high fat meal. In some embodiments, a meal is a low fat meal.

In some embodiments, the gastro-resistant pharmaceutical composition of the present disclosure is administered in combination with a gastric acid-reducing agent. For example, the subject being administered the gastro-resistant composition is also administered a regimen of a gastric acid-reducing agent. In some embodiments, the gastric-acid reducing agent is administered concomitantly with the gastro-resistant pharmaceutical composition. In some embodiments, the gastric-acid reducing agent is administered sequentially, before or after the gastro-resistant pharmaceutical composition. In some embodiments, the gastric-acid reducing agent is administered at most about 1 hour, or at most about 2 hours, or at most about 3 hours, or at most about 4 hours, or at most about 5 hours, or at most about 6 hours, or at most about 7 hours, or at most about 8 hours, or at most about 9 hours, or at most about 10 hours, or at most about 11 hours, or at most about 12 hours before the gastro-resistant formulation. In some embodiments, the gastric-acid reducing agent is administered at most about 1 hour, or at most about 2 hours, or at most about 3 hours, or at most about 4 hours, or at most about 5 hours, or at most about 6 hours, or at most about 7 hours, or at most about 8 hours, or at most about 9 hours, or at most about 10 hours, or at most about 11 hours, or at most about 12 hours after the gastro-resistant formulation.

In some embodiments, the subject being administered a combination of a gastro-resistant composition and a gastric acid reducing agent is diagnosed with or is exhibiting symptoms of acid reflux disease or gastroesophageal reflux disease (GERD). Symptoms of acid reflux disease/GERD include, but are not limited to heartburn, indigestion, regurgitation, dyspepsia, bloating, burping, dysphagia, hiccups, nausea, weight loss, wheezing, cough, hoarseness, sore throat, and intestinal bleeding.

In some embodiments, the subject being administered a combination of a gastro-resistant composition and a gastric acid reducing agent is diagnosed with or is exhibiting symptoms of esophagitis. Symptoms of esophagitis include, but are not limited to difficulties in swallowing, painful swallowing, chest pain, esophageal food impaction, heartburn, and acid regurgitation.

In some embodiments, the subject being administered a combination of a gastro-resistant composition and a gastric acid reducing agent is diagnosed with or is exhibiting symptoms of peptic ulcer disease. In some embodiments, peptic ulcer disease includes gastric ulcers. In some embodiments, peptic ulcer disease include duodenal ulcers. Symptoms of peptic ulcer disease include, but are not limited to burning stomach pain, feeling of fullness, bloating or belching, intolerance to fatty foods, heartburn, and nausea.

In some embodiments, the subject being administered a combination of a gastro-resistant composition and a gastric acid reducing agent is diagnosed with or is exhibiting symptoms of Zollinger-Ellison Syndrome. Symptoms of Zollinger-Ellison Syndrome include, but are not limited to nausea, vomiting, weight loss, diarrhea, abdominal pain, heartburn, GERD, and intestinal bleeding.

In some embodiments, the subject being administered a combination of a gastro-resistant composition and a gastric acid reducing agent is diagnosed with or is exhibiting symptoms of *Helicobacter pylori* infections. Symptoms of *Helicobacter pylori* include, but are not limited to stomach pain, nausea, loss of appetite, burping, bloating or weight loss.

In some embodiments, the subject being administered a combination of a gastro-resistant composition and a gastric acid reducing agent is administered a gastric acid-reducing agent to reduce a likelihood of occurrence of nonsteroidal anti-inflammatory drug-induced ulcers.

In some embodiments, the pharmaceutical composition is administered in the absence of a gastric acid-reducing agent. For example, the subject being administered the gastro-resistant composition is not administered a regimen of a gastric acid-reducing agent.

In some embodiments, the gastric acid-reducing agent is a proton-pump inhibitor (PPI). Non-limiting examples of proton-pump inhibitors include Omeprazole, Esomeprazole, Lansoprazole, Dexlansoprazole, Pantoprazole, and Rabeprazole.

In some embodiments, the gastric acid-reducing agent is a an antacid. Non-limiting examples of antacids include sodium bicarbonate, calcium bicarbonate, aluminum hydroxide and magnesium hydroxide.

In some embodiments, the gastric acid-reducing agent is a histamine $H_2$ receptor antagonist. Non-limiting embodiments of histamine $H_2$ receptor antagonists include Cimetidine, Ranitidine, Famotidine, and Nizatidine.

In some embodiments, the subject administered a gastro-resistant composition is diagnosed with or is exhibiting symptoms of Achlorhydria. In some embodiments, the subject administered a gastro-resistant composition is diagnosed with or is exhibiting symptoms of Hypochlorhydria. Achlorhydria or Hypochlorhydria refer to conditions in which production of hydrochloric acid in the stomach is respectively absent or reduced. Symptoms of Achlorhydria and Hypochlorhydria include, but are not limited to, epigastric pain, weight loss, heartburn, nausea, bloating, diarrhea, abdominal pain, acid regurgitation, early satiety, vomiting, postprandial fullness, constipation, Dysphagia, and Glossitis.

In some embodiments, the present disclosure provides a gastro-resistant tablet comprising a tablet core, the tablet core comprising a therapeutically-effective amount of 4-[(7-methoxy-2,3-dihydro-1,4-benzothiazepin-4(5H)yl)methyl] benzoic acid or a pharmaceutically-acceptable salt thereof as an active ingredient, a subcoating layer substantially surrounding the core, and an enteric coating, the enteric coating comprising an enteric polymer, the enteric coating substantially surrounding the subcoat.

In some embodiments, the present disclosure provides a gastro-resistant tablet comprising a tablet core, the tablet core comprising a therapeutically-effective amount of 4-[(7-methoxy-2,3-dihydro-1,4-benzothiazepin-4(5H)yl)methyl] benzoic acid hemifumarate as an active ingredient, a sub-coating layer substantially surrounding the core, and an enteric coating, the enteric coating comprising an enteric polymer, the enteric coating substantially surrounding the subcoat.

In some embodiments, the present disclosure provides a tablet comprising a core, a sub-coating layer substantially covering the core, and a coating layer substantially covering the sub-coating layer, wherein
  the core comprises 20 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
  the sub-coating layer comprises hypromellose, microcrystalline cellulose, and stearic acid; and
  the coating layer comprises hypromellose acetate succinate, triethyl citrate, sodium lauryl sulfate, and talc.

In some embodiments, the present disclosure provides a tablet comprising a core, a sub-coating layer substantially covering the core, and a coating layer substantially covering the sub-coating layer, wherein
  the core comprises 50 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
  the sub-coating layer comprises hypromellose, microcrystalline cellulose, and stearic acid; and
  the coating layer comprises hypromellose acetate succinate, triethyl citrate, sodium lauryl sulfate, and talc.

In some embodiments, the present disclosure provides a tablet comprising a core, a sub-coating layer substantially covering the core, and a coating layer substantially covering the sub-coating layer, wherein
  the core comprises 100 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
  the sub-coating layer comprises hypromellose, microcrystalline cellulose, and stearic acid; and
  the coating layer comprises hypromellose acetate succinate, triethyl citrate, sodium lauryl sulfate, and talc.

In some embodiments, the enteric polymer is hydroxypropyl methylcellulose acetate succinate (hypromellose acetate succinate, HPMC-AS), cellulose acetate phthalate, hydroxypropyl methylcellulose phthalate, cellulose acetate trimellitate, polyvinyl acetate phthalate, methacrylic acid/methacrylic acid ester copolymers (e.g., poly(methacrylic acid-co-methyl methacrylate), methacrylic acid/acrylic acid ester copolymers, or shellac (esters of aleurtic acid). In some embodiments, the enteric polymer is hydroxypropyl methylcellulose acetate succinate (hypromellose acetate succinate, HPMC-AS).

In some embodiments, the enteric coating and the subcoat each provide independently between about 0.1% and about 50% of the mass of the composition, for example, between about 0.1% and about 45%, between about 0.1% and about 40%, between about 0.1% and about 35%, between about 0.1% and about 30%, between about 0.1% and about 25%, between about 0.1% and about 20%, between about 0.1% and about 15%, between about 0.1% and about 10%, between about 0.1% and about 5%, or between about 0.1% and about 1%, by mass of the formulation.

The enteric coating and the subcoat can each independently be present at about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% by mass of the formulation.

In some embodiments, the formulation comprises about 1% to about 5% by mass of polymer in the subcoat layer. In some embodiments, the formulation comprises about 1%, about 1.5%, about 2%, about 2.5%, about 3%, about 3.5%, about 4%, about 4.5%, or about 5% or more by mass of a polymer in the subcoat layer.

In some embodiments, the formulation comprises about 5% to about 20% by mass of polymer in the enteric coating layer. In some embodiments, the formulation comprises about 5%, about 6%, about 7%, about 8%, about 9%, about 10%, about 11%, about 12%, or about 13%, about 14%, or about 15% or more by mass of a polymer in the enteric coating layer. The pharmaceutical compositions of the present disclosure comprise one or more pharmaceutically-acceptable excipients or carriers. The pharmaceutically-acceptable excipient is provided, for example, as a component of a core, subcoating, or coating layer of the composition. The pharmaceutically-acceptable excipient is, for example, compatible with the other ingredients of the composition and not deleterious to the recipient thereof.

In some embodiments, the pharmaceutical composition is in a form suitable for oral administration. Pharmaceutical compositions for solid oral administration include tablets, dragées, sublingual tablets, sachets, capsules including gelatin capsules, powders, and granules, and those for liquid oral, nasal, buccal, or ocular administration include emulsions, solutions, suspensions, drops, syrups, and aerosols. The compounds can also be administered as a suspension or solution via drinking water or with food. In some embodiments, the pharmaceutical composition is in the form of a tablet. In some embodiments, the pharmaceutical composition is in the form of a gastro-resistant tablet.

The pharmaceutically-acceptable excipient or carrier can be selected from various organic and inorganic materials that are used as materials for pharmaceutical formulations. Such materials can be incorporated as any one or more of fillers, diluents, binders, disintegrants, lubricants, glidants, plasticizers, surfactants (wetting agents), buffers (pH adjusting agents), suspending agents, colorants, emulsifiers, flavor-improving agents, gellants, preservatives, solubilizers, stabilizers, sweeteners, tonicity agents, dispersing agents, swelling agents, retardants, absorbents, and/or viscosity-increasing agents.

Non-limiting examples of pharmaceutically-acceptable fillers/diluents include cellulose derivatives including microcrystalline cellulose, silicified microcrystalline cellulose carboxymethyl cellulose, methyl cellulose, hydroxypropyl cellulose, hydroxypropyl methylcellulose (hypromellose), ethyl cellulose, starches, sugars such as mannitol, sucrose, lactose, sorbitol, or dextrins (e.g., maltodextrin), and amino-sugars.

Non-limiting examples of pharmaceutically-acceptable binders include microcrystalline cellulose, gum tragacanth, gelatin, polyvinylpyrrolidone, copovidone, hydroxypropyl methylcellulose (hypromellose), and starch.

Non-limiting examples of pharmaceutically-acceptable disintegrants include croscarmellose sodium, sodium carboxymethyl starch, and crospovidone.

Non-limiting examples of pharmaceutically-acceptable lubricants include stearates such as magnesium stearate or zinc stearate, stearic acid, sodium stearyl fumarate, talc, glyceryl behenate, sodium lauryl sulfate, polyethylene glycol, and hydrogenated vegetable oil.

Non-limiting examples of pharmaceutically-acceptable glidants include colloidal silicon dioxide, talc, tribasic calcium phosphate, calcium silicate, cellulose, magnesium silicate, magnesium trisilicate, starch, magnesium stearate, talc, and mineral oil.

Non-limiting examples of moisture barrier agents include stearic acid.

Non-limiting examples of pharmaceutically-acceptable plasticizers include trialkyl citrate, for example triethyl citrate.

Non-limiting examples of pharmaceutically-acceptable surfactants include sodium laurylsulfate or polysorbates, polyvinyl alcohol (PVA), polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid esters such as sorbitan monostearate, polyoxyethylene sorbitan fatty acid esters such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil, and hardened castor oil such as polyoxyethylene hardened castor oil.

Non-limiting examples of pharmaceutically-acceptable flavoring agents include sweeteners such as sucralose and synthetic flavor oils and flavoring aromatics, natural oils, extracts from plants, leaves, flowers, and fruits, and combinations thereof. Non-limiting examples of flavoring agents include cinnamon oils, oil of wintergreen, peppermint oils, clover oil, hay oil, anise oil, *eucalyptus*, peppermint, vanilla, citrus oil such as lemon oil, orange oil, grape and grapefruit oil, and fruit essences including apple, peach, pear, strawberry, raspberry, cherry, plum, pineapple, and apricot.

Non-limiting examples of pharmaceutically-acceptable pigments or colorants include alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide.

Non-limiting examples of buffering or pH adjusting agents include acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide, and magnesium hydroxide.

Non-limiting examples of tonicity enhancing agents include ionic and non-ionic agents such as, alkali metal or alkaline earth metal halides, urea, glycerol, sorbitol, mannitol, propylene glycol, and dextrose.

Non-limiting examples of wetting agents include glycerin, cetyl alcohol, and glycerol monostearate.

Non-limiting examples of preservatives include benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide.

Non-limiting examples of antioxidants include sorbic acid, ascorbic acid, ascorbate, glycine, α-tocopherol, butylated hydroxyanisole (BHA), and butylated hydroxytoluene (BHT).

In some embodiments, the core of the pharmaceutical composition comprises mannitol. In some embodiments, the core of the pharmaceutical composition comprises microcrystalline cellulose. In some embodiments, the core of the pharmaceutical composition comprises croscarmellose sodium. In some embodiments, the core of the pharmaceutical composition comprises magnesium stearate. In some embodiments, the core of the pharmaceutical composition comprise maltodextrin. In some embodiments, the core of the pharmaceutical composition comprises colloidal anhydrous silica. In some embodiments, the core of the pharmaceutical composition comprises sodium stearyl fumarate.

In some embodiments, the subcoat of the pharmaceutical composition comprises hydroxypropylmethylcellulose (HPMC, Hypromellose). In some embodiments, the subcoat of the pharmaceutical composition comprises microcrystalline cellulose. In some embodiments, the subcoat of the pharmaceutical composition comprises stearic acid.

In some embodiments, the enteric coating of the pharmaceutical composition comprises Hypromellose acetate succinate. In some embodiments, the enteric coating of the pharmaceutical composition comprises triethyl citrate. In some embodiments, the enteric coating of the pharmaceutical composition comprises sodium laurylsulfate. In some embodiments, the enteric coating of the pharmaceutical composition comprises talc.

A pharmaceutically-acceptable excipient can be present in a pharmaceutical composition at a mass of between about 0.1% and about 99% by mass of the composition. For example, a pharmaceutically-acceptable excipient can be present in a pharmaceutical composition at a mass of between about 0.1% and about 95%, between about 0.1% and about 90%, between about 0.1% and about 85%, between about 0.1% and about 80%, between about 0.1% and about 75%, between about 0.1% and about 70%, between about 0.1% and about 65%, between about 0.1% and about 60%, between about 0.1% and about 55%, between about 0.1% and about 50%, between about 0.1% and about 45%, between about 0.1% and about 40%, between about 0.1% and about 35%, between about 0.1% and about 30%, between about 0.1% and about 25%, between about 0.1% and about 20%, between about 0.1% and about 15%, between about 0.1% and about 10%, between about 0.1% and about 5%, between about 0.1% and about 1%, by mass of the formulation.

A pharmaceutically-acceptable excipient can be present at about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% by mass of the formulation.

In accordance with the methods of the present disclosure, any of these compounds can be administered to the subject (or are contacted with cells of the subject) in an amount effective to limit or lessen a likelihood of a decrease in the level of RyR-bound Calstabin in the subject, particularly in cells of the subject. Alternatively, the methods of the present disclosure comprise administering a compound in an amount effective to treat or lessen a likelihood of a RyR-related condition as described herein.

The pharmaceutical compositions disclosed herein are suitable for administration to human or animal subjects in a biologically compatible form suitable for administration in vivo. Subjects can be, for example, elderly adults, adults, adolescents, pre-adolescents, children, toddlers, infants, neonates, and non-human animals. In some embodiments, a subject is a patient.

Methods of Preparation

Pharmaceutical compositions described herein can be manufactured by suitable pharmacological techniques. Suitable pharmacological techniques include, e.g., one or a combination of methods such as (1) wet granulation; (2) dry granulation; (3) dry mixing; (4) direct compression; (5) milling; (6) roller compaction; or (7) fusion. Other methods include, e.g., spray drying, pan coating, melt granulation, granulation, fluidized bed spray drying or coating (e.g., wurster coating), tangential coating, top spraying, tableting, extruding and the like.

In some embodiments, a tablet disclosed herein is prepared by a wet granulation process. In wet granulation, some or all of the active ingredient(s) and excipients in powder form are blended and then further mixed in the presence of a liquid, for example water, that causes the powders to clump into granules. The granulate dried and then screened and/or milled to the desired particle size. The granulate may then be tableted, or other excipients may be added prior to tableting, such as a glidant and/or a lubricant.

In some embodiments, an active ingredient, e.g., 4-[(7-methoxy-2,3-dihydro-1,4-benzothiazepin-4(5H)yl)methyl] benzoic acid or a pharmaceutically-acceptable salt thereof is dissolved with one or more pharmaceutically-acceptable excipients, and the resulting mixture is granulated in the presence of a suitable solvent, for example water. A wet granulate is obtained which can be dried and optionally sifted to obtain a dry granulate. The dry granulate can optionally be mixed with one or more additional pharmaceutically-acceptable excipients, optionally sifted, and compressed into tablets.

In some embodiments, a tablet disclosed herein is prepared by a dry granulation process. In some embodiments, a dry granulation process is a slugging process. Slugging is a dry granulation method in which an active ingredient, optionally in combination with one or more excipients, is first compressed to form a slug and is then milled to form particulates suitable for further processing. For example, a blended composition of the active ingredient(s) and pharmaceutically-acceptable excipients may be compacted into a slug or a sheet and then ground into compacted granules. The compacted granules may subsequently be compressed into a tablet. In some embodiments, granulation of an active ingredient, e.g., 4-[(7-methoxy-2,3-dihydro-1,4-benzothiazepin-4(5H)yl)methyl] benzoic acid or a pharmaceutically-acceptable salt thereof may be accomplished by a dry granulation method.

In other embodiments, a blended composition can be compressed directly into a compacted dosage form using direct compression techniques. Direct compression produces a more uniform tablet without granules.

In some embodiments, a granulation method comprises a roller compaction method, in which powder size enlargement is accomplished by feeding an active ingredient, optionally in combination with one or more wet or dry excipients, through a roller apparatus, followed by drying (if necessary), milling, and sizing the compacted mixture to form granules having a desired particle size.

In some embodiments, a capsule described herein may comprise any of the aforementioned blends and granulates described with reference to tableting, however, they are not subjected to a final tableting step.

Pharmaceutically-Acceptable Salts

The disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a trimethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pyridazine salt, a pyrimidine salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, trifluoroacetic acid, mandelic acid, cinnamic acid, aspartic acid, stearic acid, palmitic acid, glycolic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucuronate salt, a saccharate salt, a formate salt, a benzoate salt, a glutamate salt, a pantothenate salt, an acetate salt, a trifluoroacetate salt, a mandelate salt, a cinnamate salt, an aspartate salt, a stearate salt, a palmitate salt, a glycolate salt, a propionate salt, a butyrate salt, a fumarate salt, a hemifumarate salt, a succinate salt, a methanesulfonate salt, an ethanesulfonate salt, a benzenesulfonate salt, a p-toluenesulfonate salt, a citrate salt, an oxalate salt, or a maleate salt.

Dosages and Dosing Regimens

In some embodiments, a suitable amount of 4-[(7-methoxy-2,3-dihydro-1,4-benzothiazepin-4(5H)yl)methyl] benzoic acid or a pharmaceutically-acceptable salt thereof effective to limit or lessen a likelihood of a decrease in the level of RyR-bound Calstabin in the subject and/or to treat or lessen a likelihood of conditions associated with RyR ranges from about 100 to about 500 mg per day, for example about 100 mg per day, about 110 mg per day, about 120 mg per day, about 130 mg per day, about 140 mg per day, about 150 mg per day, about 160 mg per day, about 170 mg per day, about 180 mg per day, about 190 mg per day, about 200 mg per day, about 210 mg per day, about 220 mg per day, about 230 mg per day, about 240 mg per day, about 250 mg per day, about 260 mg per day, about 270 mg per day, about 280 mg per day, about 290 mg per day, about 300 mg per day, about 310 mg per day, about 320 mg per day, about 330 mg per day, about 340 mg per day, about 350 mg per day, about 360 mg per day, about 370 mg per day, about 380 mg per day, about 390 mg per day, about 400 mg per day, about 410 mg per day, about 420 mg per day, about 430 mg per day, about 440 mg per day, about 450 mg per day, about 460 mg per day, about 470 mg per day, about 480 mg per day, about 450 mg per day, or about 500 mg per day.

In some embodiments, a suitable amount of 4-[(7-methoxy-2,3-dihydro-1,4-benzothiazepin-4(5H)yl)methyl] benzoic acid or a pharmaceutically-acceptable salt thereof effective to limit or lessen a likelihood of a decrease in the level of RyR-bound Calstabin in a subject and/or to treat or lessen a likelihood of conditions associated with RyR is about 1 mg to about 2000 mg per day; from about 1 mg to about 1000 mg per day, from about 1 mg to about 500 mg per day, from about 5 mg to about 1000 mg per day, from about 5 mg to about 500 mg per day, from about 5 mg to about 100 mg per day, from about 10 mg to about 50 mg per day, from about 50 mg to about 250 mg per day, from about 100 mg to about 200 mg per day, from about 1 mg to about 50 mg per day, from about 50 mg to about 100 mg per day, from about 100 mg to about 150 mg per day, from about 150 mg to about 200 mg per day, from about 200 mg to about 250 mg per day, from about 250 mg to about 300 mg per day, from about 300 mg to about 350 mg per day, from about 350 mg to about 400 mg per day, from about 400 mg to about 450 mg per day, from about 450 mg to about 500 mg per day, from about 500 mg to about 550 mg per day, from about 550 mg to about 600 m per day g, from about 600 mg to about 650 mg per day, from about 650 mg to about 700 mg per day, from about 700 mg to about 750 mg per day, from about 750 mg to about 800 mg per day, from about 800 mg to about 850 mg per day, from about 850 mg to about 900 mg per day, from about 900 mg to about 950 mg per day, or from about 950 mg to about 1000 mg per day.

In some embodiments, 4-[(7-methoxy-2,3-dihydro-1,4-benzothiazepin-4(5H)yl)methyl]benzoic acid or a pharmaceutically-acceptable salt thereof is present in a composition in an amount of about 1 mg, about 1.5 mg, about 2 mg, about 2.5 mg, about 3 mg, about 3.5 mg, about 4 mg, about 4.5 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 120 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg.

In some embodiments, a daily dose of 4-[(7-methoxy-2,3-dihydro-1,4-benzothiazepin-4(5H)yl)methyl]benzoic acid hemifumarate is 120 mg based on the mass of 4-[(7-methoxy-2,3-dihydro-1,4-benzothiazepin-4(5H)yl)methyl]benzoic acid. In some embodiments, a daily dose of 4-[(7-methoxy-2,3-dihydro-1,4-benzothiazepin-4(5H)yl)methyl]benzoic acid hemifumarate is 200 mg, based on the mass of 4-[(7-methoxy-2,3-dihydro-1,4-benzothiazepin-4(5H)yl)methyl]benzoic acid. In some embodiments, a daily dose of 4-[(7-methoxy-2,3-dihydro-1,4-benzothiazepin-4(5H)yl)methyl]benzoic acid hemifumarate is 141 mg. In some embodiments, a daily dose of 4-[(7-methoxy-2,3-dihydro-1,4-benzothiazepin-4(5H)yl)methyl]benzoic acid hemifumarate is 235 mg.

In some embodiments, the present disclosure provides a pharmaceutical composition comprising 20 mg 4-[(7-methoxy-2,3-dihydro-1,4-benzothiazepin-4(5H)yl)methyl]benzoic acid hemifumarate, based on the mass of 4-[(7-methoxy-2,3-dihydro-1,4-benzothiazepin-4(5H)yl)methyl]benzoic acid. In some embodiments, the present disclosure provides a pharmaceutical composition comprising in unit dosage form 23.5 mg of 4-[(7-methoxy-2,3-dihydro-1,4-benzothiazepin-4(5H)yl)methyl]benzoic acid hemifumarate.

In some embodiments, the present disclosure provides a pharmaceutical composition comprising 50 mg 4-[(7-methoxy-2,3-dihydro-1,4-benzothiazepin-4(5H)yl)methyl]benzoic acid hemifumarate, based on the mass of 4-[(7-methoxy-2,3-dihydro-1,4-benzothiazepin-4(5H)yl)methyl]benzoic acid. In some embodiments, the present disclosure provides a pharmaceutical composition comprising in unit dosage form 58.75 mg of 4-[(7-methoxy-2,3-dihydro-1,4-benzothiazepin-4(5H)yl)methyl]benzoic acid hemifumarate.

In some embodiments, the present disclosure provides a pharmaceutical composition comprising 100 mg 4-[(7-methoxy-2,3-dihydro-1,4-benzothiazepin-4(5H)yl)methyl]benzoic acid hemifumarate, based on the mass of 4-[(7-methoxy-2,3-dihydro-1,4-benzothiazepin-4(5H)yl)methyl]benzoic acid. In some embodiments, the present disclosure provides a pharmaceutical composition comprising in unit dosage form 117.5 mg of 4-[(7-methoxy-2,3-dihydro-1,4-benzothiazepin-4(5H)yl)methyl]benzoic acid hemifumarate.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg per day, about 250 mg/kg to about 2000 mg/kg per day, about 10 mg/kg to about 800 mg/kg per day, about 50 mg/kg to about 400 mg/kg per day, about 100 mg/kg to about 300 mg/kg per day, or about 150 mg/kg to about 200 mg/kg per day.

Pharmacokinetics

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein the unit dosage form is a delayed release, gastro-resistant dosage form that releases the active ingredient, 4-[(7-methoxy-2,3-dihydro-1,4-benzothiazepin-4(5H)yl)methyl]benzoic acid or a pharmaceutically-acceptable salt thereof, after a lag period of about 2-4 hours after administration. In some embodiments, the active ingredient is released from the composition in a controlled manner such that, in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 12 hours. In some embodiments, the active ingredient is released from the composition in a controlled manner such that, in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 24 hours. The pharmaceutical compositions of the present disclosure are suitable for once-daily administration.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof wherein, in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 6 hours. In some embodiments, the period of time is at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours after administration.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 6 hours after administration ($t_{max}$). In some embodiments, the present disclosure provides a pharmaceutical composition comprising in a unit dosage form 4-[(7-methoxy-2,3-dihydro-1,4-benzothiazepin-4(5H)yl)methyl]

benzoic acid or a pharmaceutically-acceptable salt thereof, wherein in a controlled study, if the unit dosage form is administered to a study subject, then a maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 5 hours after administration ($t_{max}$). In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 4 hours after administration ($t_{max}$). In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 3 to about 4 hours after administration ($t_{max}$). In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 3 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 3.5 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 4 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 4.5 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 5 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 5.5 hours after administration. In some embodiments, the maximum plasma concentration of 4-[(7-methoxy-2,3-dihydro-1,4-benzothiazepin-4(5H)yl)methyl]benzoic acid or a pharmaceutically-acceptable salt or ion thereof is reached about 6 hours after administration.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a steady-state maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 6 hours after administration ($t_{max}$). In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then steady-state a maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 5 hours after administration ($t_{max}$). In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a steady-state maximum plasma concentration ($C_{max}$) of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 4 hours after administration ($t_{max}$). In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 3 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 3.5 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 4 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 4.5 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 5 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 5.5 hours after administration. In some embodiments, the steady-state maximum plasma concentration of 4-[(7-methoxy-2,3-dihydro-1,4-benzothiazepin-4(5H)yl)methyl]benzoic acid or a pharmaceutically-acceptable salt or ion thereof is reached about 6 hours after administration. In some embodiments, the salt is a hemifumarate salt.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then an in-vivo terminal half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof of about 14 to about 21 hours is obtained in the subject. In some embodiments, the half-life of 4-[(7-methoxy-2,3-dihydro-1,4-benzothiazepin-4(5H)yl)methyl]benzoic acid or the pharmaceutically-acceptable salt or ion thereof is about 14 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 15 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 16 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 17 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 18 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 19 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 20 hours. In some embodiments, the half-life of 4-[(7-methoxy-2,3-dihydro-1,4-benzothiazepin-4(5H)yl)methyl]benzoic acid or the pharmaceutically-acceptable salt or ion thereof is about 21 hours. In some embodiments, the pharmaceutically-acceptable salt is a hemifumarate salt. In some embodiments, half-life ($t_{1/2,z}$ or $t_{1/2}$) is the terminal elimination half-life of the compound, calculated as:

$t_{1/2,z} = \ln(2)/\lambda_z$ ($\lambda_z$ being the rate constant of the terminal phase).

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then an accumulation ratio for $C_{max}$ of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio is calculated as a geometric ratio of $C_{max}$ on Day 28/$C_{max}$ on Day 1, wherein $C_{max}$ is maximum observed plasma concentration. For example, the accumulation ratio $C_{max}$ can be between about 1.4 and about 1.5, between about 1.4 and about 1.6, between about 1.4 and about 1.7, between about 1.5 and about 1.7, between about 1.5 and about 1.8, between about 1.6 and about 1.7, or between about 1.7 and about 1.8. In some embodiments, the pharmaceutically-acceptable salt is a hemifumarate salt.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then an accumulation ratio for AUC of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject. For example, the accumulation ratio AUC can be between about 1.4 and about 1.5, between about 1.4 and about 1.6, between about 1.4 and about 1.7, between about 1.5 and about 1.7, between about 1.5 and about 1.8, between about 1.6 and about 1.7, or between about 1.7 and about 1.8. In some embodiments, the pharmaceutically-acceptable salt is a hemifumarate salt. The accumulation ratio for AUC is calculated as a ratio of $AUC_{tau}$ on Day 28/$AUC_{0-24}$ Day 1, wherein:
AUC is area under the concentration-time curve;
$AUC_{tau}$ is area under the concentration-time curve during a dosing interval (tau) at steady state; and
$AUC_{0-24}$ is area under the concentration-time curve, from time 0 to 24 hours post-dose.

In some embodiments, the present disclosure provides a pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum observed plasma concentration of less than about 35 ug/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject. In some embodiments, the pharmaceutically-acceptable salt is a hemifumarate salt.

In some embodiments, the present disclosure provides a pharmaceutical composition comprising in a unit dosage form, 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum observed plasma concentration of about 10 to about 15 ng/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject after a single administration of a 120 mg dose. In some embodiments, the pharmaceutically-acceptable salt is a hemifumarate salt.

In some embodiments, the present disclosure provides a pharmaceutical composition comprising in a unit dosage form, 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a maximum observed plasma concentration of about 17 to about 21 ng/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject after 14 once-daily administrations of a 120 mg dose. In some embodiments, the pharmaceutically-acceptable salt is a hemifumarate salt.

In some embodiments, the present disclosure provides a pharmaceutical composition comprising in a unit dosage form, 4-[(7-methoxy-2,3-dihydro-1,4-benzothiazepin-4(5H)yl)methyl]benzoic acid or a pharmaceutically-acceptable salt thereof, wherein in a controlled study, if the unit dosage form is administered to a study subject, then a steady-state plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof occurs in the study subject in a range of about 3 to about 7 days after initial administration. In some embodiments, steady-state is reached after about 3 days, about 4 days, about 5 days, about 6 days, or about 7 days of once-daily administrations. In some embodiments, the pharmaceutically-acceptable salt is a hemifumarate salt.

In some embodiments, the present disclosure provides a pharmaceutical composition comprising in a unit dosage form 4-[(7-methoxy-2,3-dihydro-1,4-benzothiazepin-4(5H)

yl)methyl]benzoic acid or a pharmaceutically-acceptable salt thereof, comprising about 20 to about 200 mg of 4-[(7-methoxy-2,3-dihydro-1,4-benzothiazepin-4(5H)yl) methyl]benzoic acid hemifumarate, based on mass of 4-[(7-methoxy-2,3-dihydro-1,4-benzothiazepin-4(5H)yl)methyl] benzoic acid.

In some embodiments, the present disclosure provides a pharmaceutical composition comprising in a unit dosage form 4-[(7-methoxy-2,3-dihydro-1,4-benzothiazepin-4(5H) yl)methyl]benzoic acid or a pharmaceutically-acceptable salt thereof, comprising about 23.5 to about 235 mg of 4-[(7-methoxy-2,3-dihydro-1,4-benzothiazepin-4(5H)yl) methyl]benzoic acid hemifumarate.

In some embodiments, the present disclosure provides a pharmaceutical composition comprising in a unit dosage form 4-[(7-methoxy-2,3-dihydro-1,4-benzothiazepin-4(5H) yl)methyl]benzoic acid or a pharmaceutically-acceptable salt thereof, comprising 20 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

In some embodiments, the present disclosure provides a pharmaceutical composition comprising in a unit dosage form, 4-[(7-methoxy-2,3-dihydro-1,4-benzothiazepin-4(5H) yl)methyl]benzoic acid or a pharmaceutically-acceptable salt thereof, comprising 23.5 mg of 4-[(7-methoxy-2,3-dihydro-1,4-benzothiazepin-4(5H)yl)methyl]benzoic acid hemifumarate.

Therapeutic Use

In some embodiments, the present disclosure provides oral, modified-release formulations of 4-[(7-methoxy-2,3-dihydro-1,4-benzothiazepin-4(5H)yl)methyl]benzoic acid hemifumarate that are capable of treating conditions, disorders, and diseases associated with Ryanodine Receptors (RyRs).

In some embodiments, the present disclosure provides compounds that are RyR modulators, for example, a Rycal compound. Rycal compounds are small molecules that can, for example, bind to leaky RyR subunits, restore Calstabin binding, and repair the channel leak. In some embodiments, Rycals bind to leaky RyR channels, restore Calstabin binding, and fix the channel leak without blocking the RyR channel. In some embodiments, Rycal compounds are capable of fixing a leak in RyR channels, for example, RyR1, RyR2, and/or RyR3 channels. In some embodiments, the compositions of the disclosure enhance association and/or inhibit dissociation of RyR and Calstabin (e.g., RyR1 and Calstabin1; RyR2 and Calstabin2; and RyR3 and Calstabin1).

Non-limiting examples of conditions, disorders, and diseases associated with RyRs include disorders and diseases that can be treated and/or prevented by modulating RyRs and include, for example, a cardiac disorder or disease, a musculoskeletal disorder or disease, cancer associated muscle weakness, malignant hyperthermia, and diabetes. A compound herein can also lessen the likelihood of the occurrence of such a condition.

In some embodiments, the present disclosure provides a method of treating or reducing a likelihood of occurrence of a condition by administering to a subject in need thereof a therapeutically effective amount of a pharmaceutical composition, the pharmaceutical composition comprising 4-[(7-methoxy-2,3-dihydro-1,4-benzothiazepin-4(5H)yl)methyl] benzoic acid hemifumarate, and a pharmaceutically-acceptable excipient.

In some embodiments, the present disclosure provides a method of treating or reducing a likelihood of occurrence of a condition by administering to a subject in need thereof a modified-release pharmaceutically composition comprising a therapeutically-effective amount of 4-[(7-methoxy-2,3-dihydro-1,4-benzothiazepin-4(5H)yl)methyl]benzoic acid hemifumarate, and a pharmaceutically-acceptable excipient. In some embodiments, the composition is in solid dosage form. In some embodiments, the composition is in a form suitable for oral administration.

In some embodiments, the present disclosure provides a modified-release pharmaceutical composition comprising a therapeutically-effective amount of 4-[(7-methoxy-2,3-dihydro-1,4-benzothiazepin-4(5H)yl)methyl]benzoic acid hemifumarate, and a pharmaceutically-acceptable excipient, for use in a method of treating or reducing a likelihood of occurrence of a condition.

In some embodiments, the present disclosure provides a modified-release composition comprising a therapeutically-effective amount of 4-[(7-methoxy-2,3-dihydro-1,4-benzothiazepin-4(5H)yl)methyl]benzoic acid hemifumarate, and a pharmaceutically-acceptable excipient, for use in the manufacture of a medicament.

In some embodiments, the condition, disorder, or disease is associated with an abnormal function of RyR1. In some embodiments, the condition, disorder, or disease is associated with an abnormal function of RyR2. In some embodiments, the condition, disorder, or disease is associated with an abnormal function of RyR3.

In some embodiments, the condition is a cardiac disorder or disease. In some embodiments, the condition is a musculoskeletal disorder or disease. In some embodiments, the condition is cancer associated muscle weakness. In some embodiments, the condition is malignant hyperthermia. In some embodiments, the condition is diabetes.

Ryanodine Receptors: Excitation-Contraction Coupling (ECC) Process

The sarcoplasmic reticulum (SR) is a structure in cells that functions, among other things, as a specialized intracellular calcium ($Ca^{2+}$) store. Ryanodine receptors (RyRs) are channels in the SR, which open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability of RyRs refers to the likelihood that a RyR is open at any given moment, and therefore capable of releasing $Ca^{2+}$ into the cytoplasm from the SR.

The RyR is the major $Ca^{2+}$ release channel on the SR responsible for excitation-contraction coupling (ECC) in striated muscle. Among the three known RyR isoforms (RyR1, RyR2 and RyR3), RyR1 is widely expressed and is the predominant isoform expressed in mammalian skeletal muscle. RyR2 is also widely expressed and is the predominant form found in cardiac muscle. RyR3 expression is low in adult skeletal muscle. RyR subtypes exhibit a high degree of structural and functional homology. The subtypes form a large sarcoplasmic membrane complex, consisting of four monomers that constitute a $Ca^{2+}$ release channel associated with proteins, such as kinases, phosphatases, phosphodiesterases, and other regulatory subunits.

$Ca^{2+}$ release from the SR is modulated by several RyR binding proteins. Calmodulin, a key mediator of $Ca^{2+}$ signaling, exerts both positive and negative effects on RyR open probability. Calstabin1 (FKBP12) and calstabin2 (FKBP12.6) stabilize the closed state of RyR1 and RyR2, respectively. Calstabin1 associates predominantly with skeletal muscle RyR1, while cardiac muscle RyR2 has the highest affinity for Calstabin2.

Mutations in RYR1 or RYR2 can cause decreased binding of Calstabin1 and Calstabin2, respectively. Stress-induced post-translational modifications of RyRs including PKA phosphorylation, oxidation, and nitrosylation also can cause decreased binding of Calstabins to RyR channels. Genetic mutations and/or stress-induced posttranslational modifications of the channel can result in dissociation of Calstabin from RyRs and cause the channels to become leaky channels. The dissociation of Calstabin can lead to leaky channels, which exhibit a pathologic increase in the open probability under resting conditions. The SR $Ca^{2+}$ leak leads to a reduction in SR $Ca^{2+}$ content, with less $Ca^{2+}$ available for release and consequently weaker muscle contractions. The intracellular calcium leak has distinct pathological consequences depending on which tissue is involved.

Ryanodine Receptor 2 and Cardiac Diseases

In some embodiments, the RyR-associated condition is a cardiac disorder or disease that implicates the Ryanodine Receptor 2 (RyR2). The RyR2 channel plays a major role in intracellular calcium handling by regulating the release of $Ca^{2+}$ from the sarcoplasmic reticulum (SR) in cardiac myocytes required for ECC in cardiac muscle. The RyR2 channel is a macromolecular complex, which includes four identical RyR2 subunits, each of which binds one Calstabin2 (FKBP12.6), and other interacting proteins such as phosphatases and kinases. Binding of Calstabin2 stabilizes the channel in the closed state during the resting phase of the heart (diastole), thereby preventing diastolic calcium leak from the SR, and functionally couples groups of RyR2 channels to allow synchronous opening during excitation-contraction coupling.

Phosphorylation of RyR2 by protein kinase A (PKA) is an important part of the fight-or-flight response. Phosphorylation increases cardiac EC coupling gain by augmenting the amount of $Ca^{2+}$ released for a given trigger. The process strengthens muscle contraction and improves exercise capacity. This signaling pathway provides a mechanism by which activation of the sympathetic nervous system (SNS), in response to stress, results in increased cardiac output. Phosphorylation of RyR2 by PKA increases the sensitivity of the channel to calcium-dependent activation. The increased sensitivity leads to increased open probability and increased calcium release from the SR into the intracellular cytoplasm.

Heart failure (HF) is characterized by a sustained hyperadrenergic state in which serum catecholamine levels are chronically elevated. One consequence of this chronic hyperadrenergic state is persistent PKA hyperphosphorylation of RyR2, such that 3-4 out of the four Ser2808 in each homotetrameric RyR2 channel are chronically phosphorylated. Chronic PKA hyperphosphorylation of RyR2 is associated with depletion of the channel-stabilization subunit Calstabin2 from the RyR2 channel macromolecular complex. Depletion of Calstabin2 results in a diastolic SR $Ca^{2+}$ leak from the RyR complex, and contributes to impaired contractility. Due to the activation of inward depolarizing currents, this diastolic SR $Ca^{2+}$ leak also is associated with fatal cardiac arrhythmias. Indeed, mice engineered with RyR2 lacking the PKA phosphorylation site (RyR-S2808A) are protected from HF progression after myocardial infarction (MI). In addition, chronic PKA hyperphosphorylation of RyR2 in HF is associated with remodeling of the RyR2 macromolecular complex. The remodeling includes depletion of phosphatases PP1 and PP2a (impairing dephosphorylation of Ser2808) and the cAMP-specific type 4 phosphodiesterase (PDE4D3) from the RyR2 complex. Depletion of PDE4D3 from the RyR2 complex causes sustained elevation of local cAMP levels. Thus, diastolic SR $Ca^{2+}$ leak contributes to HF progression and arrhythmias. Additional post-translational modifications of the RyR channel (oxidation and nitrosylation) further drive the leak.

RyR leak is associated with a variety of cardiac disorders, conditions, and diseases. In some embodiments, the cardiac disorder or disease is heart failure. In some embodiments, the cardiac disorder or disease is myocardial infarction (MI). In some embodiments, the heart failure is congestive heart failure. In some embodiments, the heart failure is chronic heart failure. In some embodiments, the heart failure is systolic heart failure. In some embodiments, the heart failure is diastolic heart failure. In some embodiments, the heart failure is acute decompensated heart failure. In some embodiments, the heart failure is heart failure with reduced or preserved ejection fraction. In some embodiments, the heart failure is acute heart failure, for example, for preservation of cardiac function post myocardial infarction or cardiomyopathy.

In some embodiments, the cardiac disorder or disease comprises cardiac ischemia/reperfusion (I/R) injury. I/R injury can occur following coronary angioplasty or following thrombolysis for the treatment of myocardial infarction (MI) or during/following cardiac bypass surgery or heart transplant.

In some embodiments, the cardiac disorder or disease is characterized by an irregular heartbeat or an arrhythmia. In some embodiments, the cardiac disorder or disease is catecholaminergic polymorphic ventricular tachycardia (CPVT). In some embodiments, the cardiac disorder or disease is, or is characterized by, an atrial arrhythmia. In some embodiments, the cardiac disorder or disease is, or is characterized by, a ventricular arrhythmia. In some embodiments, the cardiac disorder or disease is, or is characterized by, atrial fibrillation. In some embodiments, the cardiac disorder or disease is, or is characterized by, ventricular fibrillation. In some embodiments, the cardiac disorder or disease is, or is characterized by, atrial tachyarrhythmia. In some embodiments, the cardiac disorder or disease is, or is characterized by, ventricular tachyarrhythmia. In some embodiments, the cardiac disorder or disease is, or is characterized by, atrial tachycardia. In some embodiments, the cardiac disorder or disease is, or is characterized by, ventricular tachycardia. In some embodiments, the cardiac disorder or disease is, or is characterized by, sick sinus syndrome. In some embodiments, the cardiac disorder or disease is, or is characterized by, Sudden infant death syndrome (SDIS). In some embodiments, the cardiac disorder or disease is, or is characterized by, sudden unexplained death (SUD).

In some embodiments, the cardiac disorder or disease is Catecholaminergic Polymorphic Ventricular Tachycardia (CPVT). In some embodiments, the cardiac disorder or disease is CPVT type 1. CPVT is one of the most lethal inherited arrhythmogenic disorders. CPVT occurs in the absence of structural heart disease and is characterized by adrenergically mediated ventricular arrhythmias associated with a high incidence of Sudden Cardiac Death (SCD). Patients usually present in the first or second decade of life with stress-induced syncope. CPVT is associated with mutations in two genes that code for proteins associated with the sarcoplasmic reticulum (SR) of the cardiomyocyte. The most frequently observed Form is CPVT type 1, an autosomal dominant form due to mutations in RyR2. This type encodes an intracellular SR calcium release channel. CPVT-associated RyR2 mutations result in leaky RyR2 channels due to the decreased binding of the Calstabin2 (FKBP12.6)

subunit, which stabilizes the closed state of the channel. Mice heterozygous for the R2474S mutation (which occurs in humans with CPVT1) in RyR2 (RyR2-R2474S mice) can exhibit exercise-induced ventricular arrhythmias and sudden cardiac death. Treatment with Rycals that enhance the binding of Calstabin2 to the mutant RyR2-R2474S channel can inhibit the channel leak and prevent cardiac arrhythmias.

Ryanodine Receptor 1 and Musculoskeletal Diseases

In some embodiments, the RyR-associated condition is a musculoskeletal disorder or disease that implicates the Ryanodine Receptor 1 (RyR1). The RyR1 macromolecular complex consists of a tetramer of the 560-kDa RyR1 subunit that forms a scaffold for proteins that regulate channel function including PKA and the phosphodiesterase 4D3 (PDE4D3), protein phosphatase 1 (PP1) and Calstabin1. A-kinase anchor protein (mAKAP) targets PKA and PDE4D3 to RyR1, whereas spinophilin targets PP1 to the channel. The catalytic and regulatory subunits of PKA, PP1, and PDE4D3 regulate PKA-mediated phosphorylation of RyR1 at Ser2843 (Ser2844 in the mouse). PKA-mediated phosphorylation of RyR1 at Ser2844 increases the sensitivity of the channel to cytoplasmic $Ca^{2+}$, reduces the binding affinity of Calstabin1 for RyR1, and destabilizes the closed state of the channel.

Calstabin1 concentrations in skeletal muscle can be approximately 200 nM. PKA phosphorylation of RyR1 can reduce the binding affinity of Calstabin1 for RyR1 from approximately 100-200 nM to more than 600 nM. Thus, under physiologic conditions, reduction in the binding affinity of Calstabin1 for RyR1, resulting from PKA phosphorylation of RyR1 at Ser2843, is sufficient to reduce substantially the amount of Calstabin1 present in the RyR1 complex. Chronic PKA hyperphosphorylation of RyR1 at Ser2843) results in leaky channels (i.e., channels prone to opening at rest), which contribute to the skeletal muscle dysfunction that is associated with persistent hyperadrenergic states such as those in individuals with heart failure.

Moreover, regulation of RyR1 by posttranslational modifications other than phosphorylation, such as by nitrosylation of free sulfhydryl groups on cysteine residues (S-nitrosylation), and channel oxidation, can increase RyR1 channel activity. S-nitrosylation and oxidation of RyR1 each can reduce Calstabin1 binding to RyR1.

In some embodiments, the musculoskeletal disorder or disease is a congenital myopathy or congenital muscular dystrophy (CMD). Congenital muscular dystrophy is present at birth. CMD is classified based on genetic mutations: 1) genes encoding for structural proteins of the basal membrane or extracellular matrix of the skeletal muscle fibers; 2) genes encoding for putative or demonstrated glycosyltransferases, that in turn affect the glycosylation of dystroglycan, an external membrane protein of the basal membrane; and 3) other. Non-limiting examples of CMD include RYR1-related myopathies (RYR1-RM), Laminin-α2-deficient CMD (MDC1A), Ullrich CMG (UCMDs 1, 2 and 3), Walker-Warburg syndrome (WWS), Muscle-eye-brain disease (MEB), Fukuyama CMD (FCMD), CMD plus secondary laminin deficiency 1 (MDC1B), CMD plus secondary laminin deficiency 2 (MDC1C), CMD with mental retardation and pachygyria (MDC1D), and Rigid spine with muscular dystrophy Type 1 (RSMD1).

In some embodiments, the musculoskeletal disease is RYR1-related congenital myopathy (RYR1-RM). RYR1-RM comprise a group of rare neuromuscular diseases. Affected individuals generally present with delayed motor milestones, muscle weakness, impaired ambulation, and, in severe cases, scoliosis, ophthalmoplegia, and respiratory distress all due to skeletal muscle weakness. Causative variants in RYR1, which encodes the major calcium ($Ca^2$) release channel in skeletal muscle, exert different effects on the RyR1 channel. The variants generally disrupt the normal $Ca^{2+}$ flow between the sarcoplasmic reticulum (SR) and muscle cell cytosol and commonly result in excessive $Ca^{2+}$ leak into the cytosol. Persistent $Ca^{2+}$ leak decreases SR $Ca^{2+}$ that is necessary for ECC. Additionally, chronic SR $Ca^{2+}$ leak results in mitochondrial calcium overload, which impairs mitochondrial function manifested as oxidative overload and reduced ATP production. SR $Ca^{2+}$ leak can also activate the calcium-activated protease calpain, which can cause cellular injury. The oxidative stress, in turn, can further contribute to RyR1 $Ca^{2+}$ leak by channel oxidation and nitrosylation.

In some embodiments, the musculoskeletal disorder or disease is muscular dystrophy. Non-limiting examples of muscular dystrophy include Duchenne Muscular Dystrophy (DMD), Becker's Muscular Dystrophy (BMD), Limb-Girdle Muscular Dystrophy (LGMD), facioscapulohumeral dystrophy, myotonic muscular dystrophy, congenital muscular dystrophy (CMD), distal muscular dystrophy, Emery-Dreifuss muscular dystrophy, and oculopharyngeal muscular dystrophy.

Duchenne muscular dystrophy (DMD) is one of the leading lethal childhood genetic diseases. Mutations in dystrophin associated with DMD lead to a complete loss of the dystrophin protein, thereby disrupting the link between the subsarcolemma cytoskeleton and the extracellular matrix. This link is essential for protecting and stabilizing the muscle against contraction induced injury. Sarcolemmal instability due to mutations in dystrophin has a cascade effect. One major effect is increased cytosolic $Ca^{2+}$ concentration, which leads to activation of $Ca^{2+}$-dependent proteases (calpains). Another effect is inflammation and elevated iNOS activity, which can cause oxidation/nitrosylation of proteins, lipids, and DNA. DMD muscle pathology is progressive and far exceeds the instability of the sarcolemma. Thus, the pathology is consistent with the instability of the sarcolemma increasing the susceptibility to further injury. Excessive oxidation or nitrosylation of RyR1 can disrupt the interaction of Calstabin1 with the RyR1 complex, leading to RyR1 leakiness and muscle weakness. Treatment with Rycals improves indices of muscle function.

In some embodiments, the musculoskeletal disorder or disease is muscle weakness associated with cancer. In some embodiments, the musculoskeletal disorder or disease is cancer cachexia, i.e., cancer associated muscle loss and/or weakness. In some embodiments, the cancer associated muscle weakness is due to bone metastases in cancer. Muscle weakness and muscle atrophy (cachexia) are common paraneoplastic conditions in cancer patients. These conditions cause significant fatigue and dramatically reduce patients' quality of life. In certain cancers, e.g., prostate and breast cancer with bone metastases, RyR1 is oxidized and becomes leaky. Repairing the leak by administration of Rycal compounds improves muscle strength and function. Non-limiting examples of cancers associated with cachexia or with muscle weakness that can be treated with a compound herein include breast cancer, prostate cancer, bone cancer, pancreatic cancer, lung cancer, colon cancer, and gastrointestinal cancer. These conditions cause significant fatigue and dramatically reduce patients' quality of life. The present disclosure provides a method for treating, preventing, and reducing a likelihood of developing muscle weakness in a cancer patient, based, for example, on the presence of a modified (e.g., an oxidized state of RyR1), which state induces RyR1 to become leaky. Prevention or reducing a likelihood of occurrence of the leak by administration of Rycal compounds can improve muscle strength and/or function.

In some embodiments, the musculoskeletal condition or disease is age-related loss of muscle mass and force (sarcopenia). Sarcopenia contributes to disability and increased mortality. RyR1 from aged mice can be oxidized, cysteine-nitrosylated, and depleted of Calstabin1, compared to RyR1 from younger (3-6 months) adults. Treating aged mice with Rycals can stabilize the binding of Calstabin1 to RyR1, reduce intracellular calcium leak, decrease reactive oxygen species (ROS), and enhance tetanic $Ca^{2+}$ release, muscle-specific force, and exercise capacity.

In some embodiments, the compositions of the present disclosure are useful in treating Type II diabetes by reducing a likelihood of occurrence of intracellular calcium leak via leaky RyR2. This leak causes mitochondrial calcium overload, and decreased ATP production, which reduces activation of $K_{ATP}$ channels. Reduced activation of the channels blocks depolarization of the plasma membrane. This blocking decreases activation of the plasma membrane voltage-gated calcium channel, which is the primary source of calcium required for insulin secretion.

Example 1: Gastro-Resistant Tablet (Formulation A)

A gastro-resistant tablet comprising 20, 40, or 200 mg 4-[(7-methoxy-2,3-dihydro-1,4-benzothiazepin-4(5H)yl)methyl]benzoic acid hemifumarate (Compound I) (based on the mass of 4-[(7-methoxy-2,3-dihydro-1,4-benzothiazepin-4(5H)yl)methyl]benzoic acid) is provided in Table 1.

Preparation Method: Compound I was mixed with cellulose microcrystalline, povidone and crospovidone. The mixture was granulated using a standard wet granulation process. Polysorbate was added to purified water to function as a granulation fluid. The wet granulate was dried in an oven system and sifted. The dry granulate was mixed with the external phase: crospovidone, magnesium stearate, and silica colloidal anhydrous, and the lubricated granulate was sifted and compressed into tablets.

Subsequently, the core tablets were coated with a premix (white Sepifilm LP 770) (sub-coating). After drying, the enteric coating is applied as an AQOAT suspension to obtain gastro-resistant tablets.

Example 2: Gastro-Resistant Tablet (Formulation B1)

A gastro-resistant tablet comprising 20 mg 4-[(7-methoxy-2,3-dihydro-1,4-benzothiazepin-4(5H)yl)methyl]benzoic acid hemi-fumarate (Compound I) (based on the mass of 4-[(7-methoxy-2,3-dihydro-1,4-benzothiazepin-4(5H)yl)methyl]benzoic acid) is provided in Table 2.

TABLE 2

Gastro-Resistant Tablet

| | Component | Quantity (mg) | Ratio (%) |
|---|---|---|---|
| Core | Compound I | 23.52 | 47.04 |
| | Corresponding in base to | 20 | |
| | Cellulose, microcrystalline | 7.65 | 15.3 |
| | Croscarmellose sodium | 2.20 | 4.4 |
| | Maltodextrin | 5.75 | 11.5 |

TABLE 1

Gastro-Resistant Tablet

| | | Quantity/Unit (mg/tablet) | | |
|---|---|---|---|---|
| | Component | 20 mg | 40 mg | 200 mg |
| Intra-granular | Compound I | 23.52 | 47.04 | 235.20 |
| | Corresponding in base to | 20 | 40 | 200 |
| | Cellulose, microcrystalline | 8.48 | 16.96 | 84.82 |
| | Povidone (PVP K17) | 5.20 | 10.40 | 52.00 |
| | Crospovidone | 1.00 | 2.00 | 10.00 |
| | Polysorbate 80 | 0.12 | 0.24 | 1.18 |
| | Purified water | q.s. | q.s. | q.s. |
| Extra-granular | Crospovidone | 1.20 | 2.40 | 12.00 |
| | Magnesium stearate | 0.40 | 0.80 | 4.00 |
| | Silica, colloidal anhydrous | 0.08 | 0.16 | 0.80 |
| | Weight of tablet core (mg) | 40 | 80 | 400 |
| Sub-coating | White Sepifilm LP 770, containing: | Target 3%* | Target 3%* | Target 3%* |
| | Hypromellose | 0.78 | 1.56 | 7.80 |
| | Cellulose, microcrystalline | 0.12 | 0.24 | 1.20 |
| | Stearic acid | 0.12 | 0.24 | 1.20 |
| | Titanium dioxide E171 | 0.18 | 0.36 | 1.80 |
| | Purified water | q.s.*** | q.s. | q.s. |
| Enteric Coating | AQOAT suspension, containing: | Target 21%** | Target 17%** | Target 10%** |
| | Hypromellose acetate succinate (HPMCAS-LF) | 5.49 | 8.89 | 26.14 |
| | Triethyl citrate | 1.10 | 1.78 | 5.23 |
| | Sodium laurilsulfate | 0.16 | 0.27 | 0.78 |
| | Talc | 1.65 | 2.67 | 7.84 |
| | Purified water | q.s. | q.s. | q.s. |
| | Total Weight of tablets (mg) | 49.6 | Approx. 96 | Approx. 452 |

*Target mass of coating applied to core tablets. Coating is applied as an 11.2% suspension in purified water containing: hypromellose 65.0%, cellulose microcrystalline 10.0%, stearic acid 10.0%, and titanium dioxide E171 15.0%.
**Target mass of coating applied to core tablets. Coating is applied as a 7% AQOAT suspension in purified water containing: hypromellose acetate succinate (HPMCAS-LF) 7.0%, triethyl citrate 1.40%, sodium laurilsulfate 0.21%, and talc 2.10%.
***q.s. is quantum sufficit ("as much as is sufficient").

TABLE 2-continued

Gastro-Resistant Tablet

| | Component | Quantity (mg) | Ratio (%) |
|---|---|---|---|
| | Magnesium stearate | 0.40 | 0.8 |
| | Silica, colloidal anhydrous | 0.08 | 0.16 |
| | Sodium stearyl fumarate | 0.40 | 0.8 |
| | Weight of tablet core (mg) | 40.0 | |
| Sub-coating | Colorless Sepifilm LP 010, | Target 3%** | |
| | Hypromellose | 0.96 | 1.92 |
| | Cellulose, microcrystalline | 0.12 | 0.24 |
| | Stearic acid | 0.12 | 0.24 |
| | Purified water | q.s.*** | |
| Enteric Coating | AQOAT suspension, | Target 22%*** | |
| | Hypromellose acetate succinate (HPMCAS-MF) | 5.49 | 10.98 |
| | Triethyl citrate | 1.54 | 3.08 |
| | Sodium laurilsulfate | 0.16 | 0.32 |
| | Talc | 1.65 | 3.33 |
| | Purified water | q.s. | |
| | Total | 50.0 | 100 |

*Target mass of coating applied to core tablets. Coating is applied as an 11.2% suspension in purified water containing: hypromellose 80.0%, cellulose microcrystalline 10.0%, Stearic acid 10.0%.
**Target mass of coating applied to core tablets. Coating is applied as a 7% AQOAT suspension in purified water containing: hypromellose acetate succinate (HPMCAS-MF) 7.0%, Triethyl citrate 1.96%, Sodium laurilsulfate 0.21%, and Talc 2.10%.
***q.s. is quantum sufficit ("as much as is sufficient").

Preparation Method: Compound I was mixed with microcrystalline cellulose, maltodextrin and croscarmellose. The mixture was granulated via a standard wet granulation process. Purified water was added as granulation fluid. The wet granulate was dried in an oven system and sifted. The dry granulate was mixed with the external phase: croscarmellose, magnesium stearate, sodium stearyl fumarate, and silica colloidal anhydrous, and the lubricated granulate is sifted and compressed into tablets.

Subsequently, the core tablets were coated with a premix (colorless Sepifilm LP 010) (sub-coating). After drying, the enteric coating as applied as an AQOAT suspension to obtain gastro-resistant tablets.

Example 3: Gastro-Resistant Tablet (Formulation B2)

A gastro-resistant tablet comprising 20 mg 4-[(7-methoxy-2,3-dihydro-1,4-benzothiazepin-4(5H)yl)methyl] benzoic acid hemi-fumarate (Compound I) (based on the mass of 4-[(7-methoxy-2,3-dihydro-1,4-benzothiazepin-4 (5H)yl)methyl]benzoic acid) is provided in Table 3.

TABLE 3

Gastro-Resistant Tablet

| | Component | Quantity (mg) | Ratio (%) |
|---|---|---|---|
| Core | Compound I | 23.52 | 38.18 |
| | Corresponding in base to | 20 | |
| | Mannitol | 6.78 | 11.01 |
| | Cellulose, microcrystalline | 10.00 | 16.23 |
| | Croscarmellose sodium | 1.50 | 2.44 |
| | Magnesium stearate | 0.50 | 0.81 |
| | Maltodextrin | 7.10 | 11.53 |
| | Silica, colloidal anhydrous | 0.10 | 0.16 |
| | Sodium stearyl fumarate | 0.50 | 0.81 |
| | Weight of tablet core | 81.17 | 50 |
| Sub-coating | Colourless Sepifilm LP 010: | — | 3* |
| | Hypromellose | 1.20 | 1.94 |
| | Cellulose, microcrystalline | 0.15 | 0.24 |

TABLE 3-continued

Gastro-Resistant Tablet

| | Component | Quantity (mg) | Ratio (%) |
|---|---|---|---|
| | Stearic acid | 0.15 | 0.24 |
| | Purified water | q.s.*** | q.s. |
| Enteric Coating | AQOAT suspension: | | 20.2** |
| | Hypromellose acetate succinate | 6.27 | 10.18 |
| | Triethyl citrate | 1.75 | 2.85 |
| | Sodium laurilsulfate | 0.18 | 0.31 |
| | Talc | 1.88 | 3.06 |
| | Purified water | q.s. | q.s. |
| | Total | 61.6 | 100.0 |

*Target mass of coating applied to core tablets. Coating is applied as an 11.2% suspension in purified water containing: hypromellose 80.0%, cellulose microcrystalline 10.0% and stearic acid 10.0%.
**Target mass of coating applied to core tablets. Coating is applied as a 7% AQOAT suspension in purified water containing: Hypromellose acetate succinate (HPMCAS-MF) 7.0%, triethyl citrate 1.96%, sodium laurylsulfate 0.21%, and talc 2.10%.
***q.s. is quantum sufficit ("as much as is sufficient").

Preparation Method: Compound I was mixed with mannitol, cellulose microcrystalline, and maltodextrin. The mixture is granulated via a standard wet granulation process. The obtained wet granulate was dried and sifted. Then, the dry granulate was mixed with croscarmellose, magnesium stearate, silica colloidal anhydrous, and sodium stearyl fumarate. The lubricated granulate was sifted and compressed into tablets.

Subsequently, the core tablets were coated with sub-coating (colourless Sepifilm LP 010). After drying, the enteric coating was applied (AQOAT suspension AS-MF) to obtain enteric-coated tablets.

Example 4: Placebo

A placebo, enteric-coated tablet formulation is provided in Table 4.

TABLE 4

Placebo

| Ingredients | Amount (g) |
|---|---|
| TABLET CORE | |
| Lactose monohydrate | 30 |
| Microcrystalline cellulose | 19.5 |
| Magnesium stearate | 0.5 |
| For an uncoated tablet with a mass of | 50 |
| SUB-COATING | |
| Sepifilm LP 010, containing*: | |
| Hypromellose 6 cps | 3.9 |
| Hypromellose 15 cps | 1.7 |
| Cellulose microcrystalline | 0.7 |
| Stearic acid | 0.7 |
| ENTERIC COATING | |
| AQOAT suspension, containing**: | |
| Hypromellose acetate succinate (HPMCAS-LF) | 2.7 |
| Triethyl citrate | 0.8 |
| Sodium Lauryl sulphate | 0.1 |
| Talc | 0.8 |
| INTERMEDIARY VEHICLE | |
| Water, purified | q.s |
| For an enteric-coated tablet finished with a mass | 61.6 |

*Coating is applied as an 11.2% sepifilm suspension in purified water containing: hydroxypropylmethyl cellulose (hypromellose) 6 cps 56.0%, hydroxypropylmethyl cellulose 15 cps 24.0%, microcrystalline cellulose 10.0%, stearic acid 10.0%
**Coating is applied as a 7% AQOAT suspension in purified water containing Hypromellose acetate succinate (HPMCAS-LF) 7.0%, Triethyl citrate 2.0%, Sodium Lauryl sulphate 0.21% and Talc 2.10%.

Preparation Method: Lactose monohydrate and cellulose microcrystalline were mixed. Then magnesium stearate was added. Subsequently, the core tablets were coated with sub-coating (colorless Sepifilm LP 010). After drying, the enteric coating was applied (AQOAT suspension AS-MF) to obtain enteric-coated tablets.

Example 5: Dissolution Studies

Dissolution studies were used to compare the tablets of Example 2 and Example 3. Since the gastro-resistant oral tablets are designed to remain intact in the stomach and then to release the active substance along the gastrointestinal tract, dissolution under acidic conditions (pH 1.2) for 2 hours followed by near-neutral medium (e.g. pH 6.8) was assessed. Furthermore, to assess dissolution conditions representative of a fed state (e.g., when a subject is administered a formulation during or shortly after a meal), dissolution was evaluated at a higher pH (e.g. in the range 3-5). Thus, dissolution under pH 4.5 for 2 h followed by near-neutral medium (e.g. pH 6.8) were performed.

This test was performed to determine the fraction of the drug substance released from the enteric-coated tablets in the dissolution mediums at a specified period of time for each individual tablet tested.

Dissolution conditions are provided in Table 5.

TABLE 5

Dissolution conditions

| Parameters | Conditions |
|---|---|
| Apparatus | Paddle dissolution apparatus, as described in the European Pharmacopoeia, (2.9.3.) |
| Temperature of the dissolution medium | 37.0° C. ± 0.5° C. |
| Paddle rotation speed | 75 rpm ± 3 rpm |
| Dissolution media | Acid stage: 750 mL of HCl 0.1N degassed (medium 1) Buffer pH 6.8 stage (phosphate buffer): Add 250 mL of concentrate at 37° C. adjust within 5 minutes to pH 6.8 ± 0.05 with HCl 2M or NaOH 2M (medium 2) |
| Dissolution volume | 750 ml ± 7.5 ml for acid stage (medium 1) 1000 mL ± 10 mL for buffer stage (medium 2) |
| Sampling mode | automatic (or equivalent) |
| Sampling volume | 1 mL for HPLC analysis and 10 mL for UV analysis |
| Sampling Times | Acidic stage: 0 and 120 min Buffer pH 6.8 stage: 125, 130, 135, 150, 165, 180, and 195 minutes (corresponding to 5, 10, 15, 30, 45, 60, and 75 minutes) 5, 10, 15, 30, 60 and 75 min for information results. 120 min sample of the acidic stage is analyzed as the T0 of the pH = 6.8 buffer stage. All test times stated are to be observed within a tolerance of ±2% |
| Filtration | glass microfibre filters 2.7 μm (Whatman-GF/D-2.7 μm-Ø 25 mm or equivalent) |

Analysis Conditions

The drug substance released from the units is assayed by ultraviolet spectrophotometry in following conditions:

Quartz cell optical path length: 10 mm

Absorbance wavelength: 250 nm

Reference wavelength: 350 nm

The disintegration time is determined by incubating the tablet in 0.1 N hydrochloric acid as the liquid medium, for two hours (pH=1.2); or a pH 4.5 buffer for 2 hours, then replacing the acid by phosphate buffer solution pH 6.8 for 60 minutes.

Drug substance release profiles were evaluated in vitro using paddle dissolution apparatus (75±3 rpm, 37.0±0.5° C.). Samples were withdrawn at regular intervals and then analyzed by ultraviolet spectrophotometry at 250 nm and 350 nm. The in vitro dissolution-time profiles obtained are reported in FIG. 1.

According to these in vitro data, similar dissolution profiles were obtained with formulations of Example 2 (20 mg/formulation B1) and Example 3 (20 mg/Formulation B2).

Figure 2:
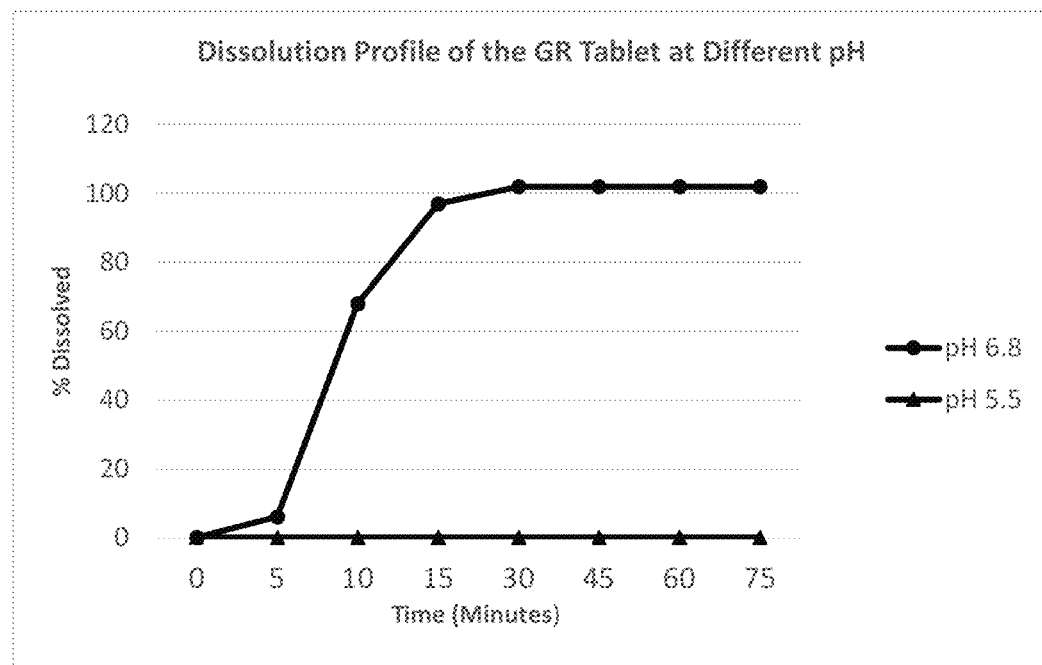
FIG. 2: In vitro dissolution time profiles of gastro-resistant tablets of Example 2 (pH 6.8, •) and Example 3 (pH 5.5, ▲).

In-vitro dissolution time profiles of formulations of Example 2 at a pH or 6.8 and of Example 3 at pH of 5.5 are shown in FIG. 2.

According to these in vitro data, a pH value at dosing time equal to or lower than 5.5 preserves the integrity of the gastro-resistant form. The tablet rapidly disintegrates at a pH of 6.8.

Example 6: Clinical Trial in Healthy Volunteers

A Phase 1, randomized, double-blind, placebo-controlled clinical trial was performed to assess the safety and pharmacokinetics (PK) of Compound I after single, escalating, and repeated oral doses in health male volunteers.

Study Objectives

Part I (Single Ascending Doses—SAD)

The primary objective was to assess the safety of escalating single oral doses of Compound I compared with placebo in healthy male volunteers. The secondary objective was to measure plasma pharmacokinetic (PK) parameters of Compound I.

Part II (Multiple Ascending Doses—MAD)

The primary objective was to assess the safety of escalating repeated oral doses of Compound I over 14 days compared with placebo in healthy male volunteers. The secondary objective was to measure plasma pharmacoki netic (PK) parameters of Compound I and to assess the concentration of Compound I in quadriceps muscle.

Materials and Methods

1. Study Drug

4-[(7-methoxy-2,3-dihydro-1,4-benzothiazepin-4(5H)yl) methyl]benzoic acid hemi-fumarate (Compound I) was administered in a gastro-resistant tablet according to Example 1. The formulation contained 20 mg, 40 mg, or 200 mg Compound I (based on the mass of 4-[(7-methoxy-2,3-dihydro-1,4-benzothiazepin-4(5H)yl)methyl]benzoic acid). Placebo tablet according to Example 4 was used as comparator.

2. Study Design

The study was subdivided into two parts (I and II). Each part was randomized, double-blind, placebo-controlled.

In part I, participants from groups A, B, C, D, and E received single doses of 40 mg, 80 mg, 160 mg, 240 mg, or 400 mg Compound I, respectively, or corresponding placebo. Forty subjects completed part I: 30 active (6 per cohort) and 10 placebo.

In Part II, participants from groups I, J, K, and L received repeated doses of 20 mg, 60 mg, 120 mg, or 240 mg Compound I, respectively, or corresponding placebo once daily over a period of 14 days. Forty-one subjects completed Part II: 7/7/8/7 for cohorts I, J, K, L, and twelve placebo.

3. Pharmacokinetic Measurements

3a. Blood Sampling:

In Part I, blood samples were collected from each participant as follows: at pre-dose, then 0.25, 0.5, 1, 1.5, 2, 3, 4, 5, 6, 8, 10, 12, 16, 24, 36, 48, 60, 72, and 96 hours after dosing.

In Part II, blood samples were collected from each participant as follows: Day 1: 12 samples from the pre-morning dose up to 16 h (pre-dose, 0.25, 0.5, 1, 1.5, 2, 3, 4, 6, 8, 12, and 16 h), Days 2-13: 12 samples at pre-doses (i.e., morning dose); Day 14: 16 samples from the pre-morning dose up to 96 (D14 pre-dose, 0.25, 0.5, 1, 1.5, 2, 3, 4, 6, 8, 12, and 16 h and D15-18: 1 sample before theoretical morning dosing.

The following pharmacokinetic parameters were calculated from plasma concentration time profiles:

$AUC_{last}$ (AUClast): area under the concentration-time curve from time zero (time of drug administration) to $t_{last}$ AUC: area under the concentration-time curve from time zero (time of drug administration) to infinity $AUC_{24}$ (AUC24): area under the concentration-time curve from time zero to 24 h on Day 1.

$AUC_\tau$ ($AUC_{tau}$): area under the concentration-time curve over the dosing interval at steady state on Day 14.

$C_{max}$ (Cmax): maximum observed concentration $C_{maxds}$ (Cmaxds): $C_{max}$/dose $t_{max}$ (tmax): time corresponding to $C_{max}$ $t_{lag}$ (tlag) lag time: time prior to the time corresponding to the first measurable concentration $C_{last}$ (Clast): last quantifiable observed concentration $R_{ac(AUC\tau)}$ (RacAUC): accumulation ratio of AUC ($AUC_\tau$/$AUC_{24}$)

$R_{acCmax}$ (RacCmax): accumulation ratio of $C_{max}$ ($C_{max}$ Day 14/$C_{max}$ Day 1)

$t_{last}$ (tlast): time corresponding to $C_{last}$ $\lambda_z$ (k): first order rate constant of the terminal phase $t_{1/2,z}$ (t1/2): terminal elimination half-life of the compound, calculated as:

$t_{1/2,z} = \ln(2)/\lambda_z$ ($\lambda_z$ being the rate constant of the terminal phase).

The area under the plasma concentration-time curve was calculated using a combined linear and logarithmic trapezoidal rule. The interpolation was linear in the constant and ascending parts of the plasma concentration-time profiles. The interpolation was logarithmic in the descending parts.

For Part I, to assess the dose effect on the PK of Compound I, the mean $AUC_{last}$ and $C_{max}$ for each dose were calculated and were plotted by dose.

For Part II, the same approach was used on $AUC_\tau$ (Day 14) respectively $AUC_{24}$ (Day 1), and $C_{max}$.

3b. Muscle Biopsy

For Study part II (for all groups), Concentrations of Compound I were determined in muscle by performing muscle biopsy on quadriceps muscle on day 13, at least 3 hours after morning dose.

3c. Statistical Methods:

For each group and treatment, descriptive statistics (N, arithmetic mean, standard deviation, minimum, median, maximum, coefficient of variation, geometric mean, and geometric CV, as appropriate) were calculated for the concentrations and pharmacokinetic parameters of Compound I.

3d. Analytical Methods:

Plasma and muscle samples were analyzed by LC-MS/MS method.

Results

1. Pharmacokinetics

1a. Part I: Single Ascending Dose

Figure 3:
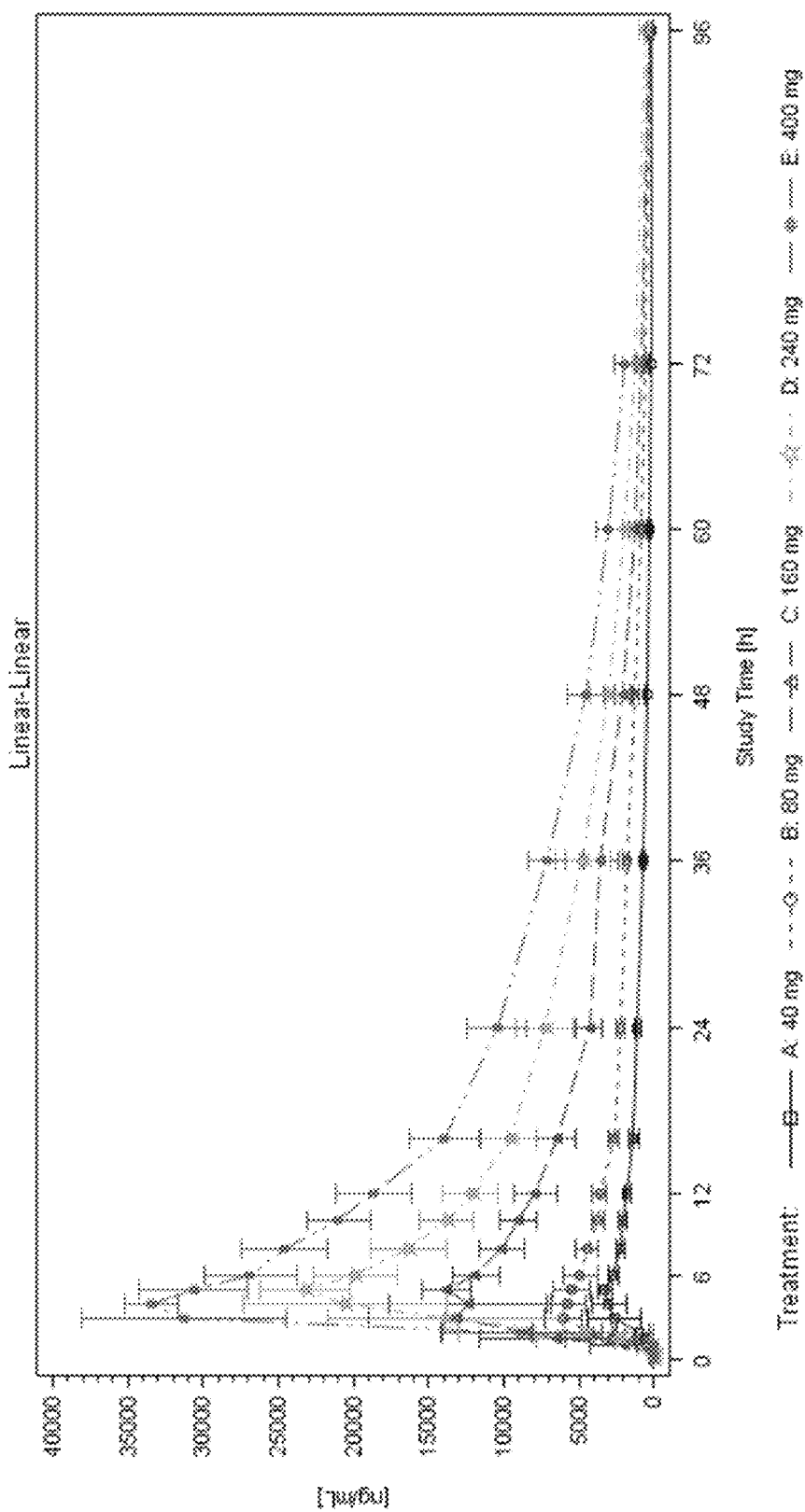
FIG. 3: Mean plasma concentration (+/−SD) time profile of Compound I on Day 1 (Part I: single dose, healthy volunteers), in ng/mL.

Mean concentration time profiles of Part I (single dose) are shown in FIG. 3. Concentrations are shown in ng/mL.

Table 6 summarizes pharmacokinetic parameters after a single dose (arithmetic and geometric means, standard deviation (SD), coefficient of variation (CV %) and geometric CV %, median and range).

TABLE 6

Part I: $AUC_{last}$, AUC, $C_{max}$, and $t_{max}$ on Day 1

| Part I Parameter/Unit | Treatment A (n = 6)/40 mg Geom. Mean (geom. % CV) | Treatment B (n = 6)/80 mg Geom. Mean (geom. % CV) | Treatment C (n = 6)/160 mg Geom. Mean (geom. % CV) | Treatment D (n = 6)/240 mg Geom. Mean (geom. % CV) | Treatment E (n = 6)/400 mg Geom. Mean (geom. % CV) |
|---|---|---|---|---|---|
| $AUC_{last}$ ng*h/mL | 68658 (16.3) | 152782 (6.8) | 303849 (19.7) | 450902 (20.9) | 656199 (12.0) |
| AUC ng*h/mL | 71710 (17.8) | 162902 (7.3) | 312443 (20.5) | 463877 (23.0) | 708394 (14.0) |
| $C_{max}$ ng/mL | 3940 (3.4) | 6883 (32.4) | 15490 (13.1) | 24461 (8.5) | 35101 (5.8) |

TABLE 6-continued

| | Part I: AUC$_{last}$, AUC, C$_{max}$, and t$_{max}$ on Day 1 | | | | |
|---|---|---|---|---|---|
| Part I Parameter/Unit | Treatment A (n = 6)/40 mg Geom. Mean (geom. % CV) | Treatment B (n = 6)/80 mg Geom. Mean (geom. % CV) | Treatment C (n = 6)/160 mg Geom. Mean (geom. % CV) | Treatment D (n = 6)/240 mg Geom. Mean (geom. % CV) | Treatment E (n = 6)/400 mg Geom. Mean (geom. % CV) |
| t$_{1/2, z}$ h | 20.9 (12.3) | 22.7 (15.4) | 17.5 (14.6) | 17.7 (16.8) | 18.7 (12.6) |
| t$_{max}$# h | 3.00 (2.0-5.0) | 3.00 (1.5-12.0) | 3.00 (2.0-5.0) | 4.50 (2.0-5.0) | 3.50 (3.0-5.0) | median and range

1b. Part II: Multiple Ascending Dose

Figure 4:
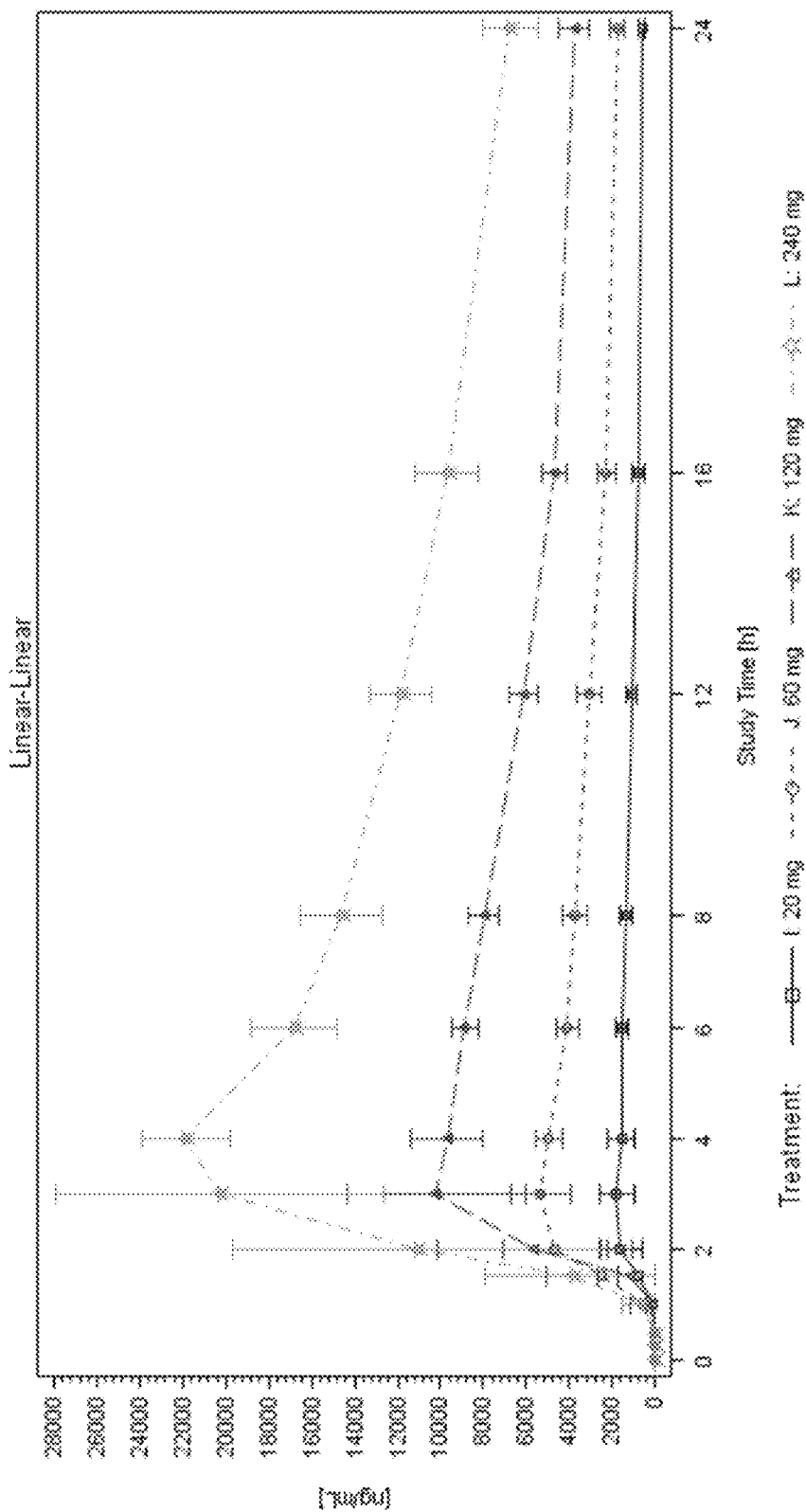
FIG. 4: Mean plasma concentration (+/−SD) time profile of Compound I on Day 1 (Part II: repeated doses, healthy volunteers), in ng/mL.

Mean concentration time profiles of Part II (repeated doses) on day 1 are shown in FIG. 4. Concentrations are shown in ng/mL.

Figure 5:
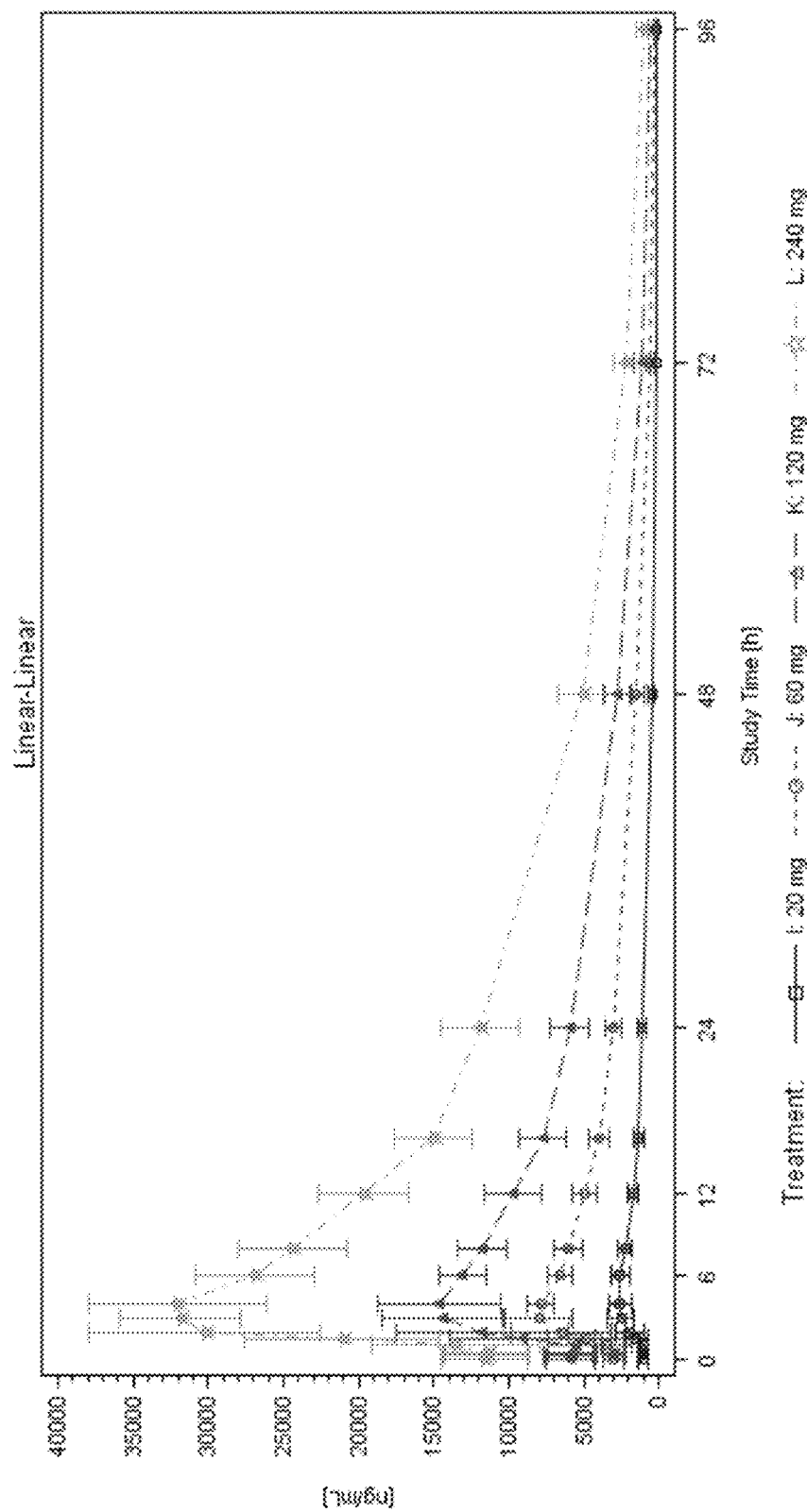
FIG. 5: Mean plasma concentration (+/−SD) time profile of Compound I on Day 14 (Part II: repeated doses, healthy volunteers), in ng/mL.

Mean concentration time profiles of Part II (repeated doses) on day 14 are shown in FIG. 5. Concentrations are shown in ng/mL.

Table 7 summarizes pharmacokinetic parameters after repeated doses (arithmetic and geometric means, SD, CV % and geometric CV %, median and range).

TABLE 7

| | | Part II: AUC$_{0-24}$, AUC$_\tau$, C$_{max}$, and t$_{max}$ on Day 1 and on Day 14 | | | |
|---|---|---|---|---|---|
| Part II, Day 1 and Day 14 Parameter | Unit | Treatment I (n = 7)/20 mg Geom. Mean (geom. % CV) | Treatment J (n = 7)/60 mg Geom. Mean (geom. % CV) | Treatment K (n = 8)/120 mg Geom. Mean (geom. % CV) | Treatment L (n = 7)/240 mg Geom. Mean (geom. % CV) |
| | | | Day 1 | | |
| AUC$_{0-24}$ | ng*h/mL | 24342 (19.3)* | 69212 (16.5) | 138083 (10.5) | 270249 (13.0) |
| C$_{max}$ | ng/mL | 2201 (20.4) (n = 8) | 6091 (14.4) | 11478 (11.1) | 23863 (7.9) |
| t$_{max}$# | h | 2.52 (2.0-6.0) (n = 8) | 3.00 (1.5-4.0) | 3.00 (2.0-6.0) | 3.00 (3.0-4.0) |
| | | | Day 14 | | |
| AUC$_\tau$ | ng*h/mL | 40124 (21.3) | 115218 (19.7) | 220525 (22.3) | 464565 (14.0) |
| C$_{max}$ | ng/mL | 3107 (13.6) | 8835 (12.7) | 16341 (17.6) | 34852 (14.7) |
| t$_{1/2, z}$ | h | 19.3 (22.2) | 19.7 (15.4) | 19.3 (19.8) | 19.8 (11.3) |
| Rac$_{(AUC\tau)}$ | — | 1.65 (15.4) | 1.66 (12.5) | 1.60 (12.8) | 1.72 (10.5) |
| Rac$_{(Cmax)}$ | — | 1.39 (17.3) | 1.66 (12.5) | 1.42 (8.8) | 1.46 (13.6) |
| t$_{max}$# | h | 3.00 (1.5-6.0) | 1.45 (15.1) | 3.50 (1.5-6.0) | 3.00 (2.0-4.0) | median and range
*n = 7, one withdrawn subject

2. Muscle Biopsy

Muscle biopsy was performed to assess the concentration of Compound I in quadriceps muscle. The biopsy was performed on Day 13 at 3 hours post dose at least.

Table 8 shows the concentrations of Compound I in the muscle summarized by medians and ranges.

TABLE 8

| | | Concentrations of Compound I in quadriceps muscle (unbound and total) | | | |
|---|---|---|---|---|---|
| Part II Parameter | Unit | Treatment I (n = 7)/20 mg Median (Range) | Treatment J (n = 7)/60 mg Median (Range) | Treatment K (n = 8)/120 mg Median (Range) | Treatment L (n = 7)/240 mg Median (Range) |
| Unbound Cpd I concentration | ng/g | 22.0 (17.5-41.5) | 80.3 (49.7-124) | 104 (63.2-196) | 242 (196-452) |
| Total Cpd I concentration | ng/g | 171 (141-341) | 489 (273-693) | 913 (614-1207) | 1480 (890-1745) |

Table 9 summarizes the ratios of unbound respective total concentration at Day 13 at 3 hours post dose divided by the plasma concentration on Day 14 at 3 hours post dose.

TABLE 9

Ratios of Compound I concentrations in quadriceps muscle (unbound and total) divided by plasma concentrations

| Part II Parameter | Unit | Treatment I (n = 7)/20 mg Geom. Mean (geom. % CV) | Treatment J (n = 7)/60 mg Geom. Mean (geom. % CV) | Treatment K (n = 8)/120 mg Geom. Mean (geom. % CV) | Treatment L (n = 7)/240 mg Geom. Mean (geom. % CV) |
|---|---|---|---|---|---|
| Kp | (ng/g)/(ng/mL) | 0.0808 (65.3) | 0.0640 (22.6) | 0.0636 (49.9) | 0.0440 (30.0) |
| Kpu | (ng/g)/(ng/mL) | 0.0106 (59.2) | 0.0100 (31.3) | 0.0081 (60.7) | 0.0081 (32.5) |

3. Discussion:

Part I: After single oral administration in young healthy males of 20, 40, 80, 160, 240, and 400 mg of 4-[(7-methoxy-2,3-dihydro-1,4-benzothiazepin-4(5H)yl)methyl]benzoic acid hemifumarate, rapid absorption was observed, after a lag time consistent with the gastro-resistant (GR) properties of the tablet administered. No evidence of non-linearity with the dose was observed. The inter-individual variability across treatment groups was low. Geometric mean $t_{1/2,z}$ ranged from 17.5 h in the 160 mg cohort to 22.7 h in the 80 mg cohort while the geometric % CV ranged from 12.3% to 16.8%. Graphical inspections show dose proportionality with regard to $AUC_{last}$ and $C_{max}$.

Part II: After 14-days of repeated once daily oral administrations of 20 mg of 4-[(7-methoxy-2,3-dihydro-1,4-benzothiazepin-4(5H)yl)methyl]benzoic acid hemifumarate, $C_{max}$ was reached with a median $T_{max}$ between 3 and 3.5 hours. Steady-state was attained after 3-7 days of daily treatment (e.g., at day 4 in the 20, 60, and 120 mg cohorts and at day 5 in the 240 mg cohort). The geometric % CV for the AUC on Days 1 and 14 ranged from 10.5% (120 mg cohort, Day 1) to 22.3% (120 mg cohort, Day 14). The inter-individual variability across treatment groups was low. Geometric mean $t_{1/2,z}$ at Day 14 ranged from 19.3 h in the 20 and 120 mg cohorts to 19.8 h in the 240 mg cohort. The % CV ranged from 11.3% to 22.2%. Graphical inspections showed dose proportionality regarding $AUC_{\tau}$ resp. $AUC_{0-24}$ and $C_{max}$. Geometric mean accumulation ratios based on AUC ranging from 1.60 to 1.72 and on $C_{max}$ ranging from 1.39 to 1.46 appeared similar across dose groups.

The median unbound and total 4-[(7-methoxy-2,3-dihydro-1,4-benzothiazepin-4(5H)yl)methyl]benzoic acid hemifumarate concentrations in quadriceps muscle appeared dose proportional. The geometric mean ratios of concentrations in muscle divided by plasma concentrations ranged from 0.0440 to 0.0808 (ng/g)/(ng/mL) for Kp and from 0.0081 to 0.0106 (ng/g)/(ng/mL) for Kpu. The geometric % CVs ranged from 22.6% to 65.3% for Kp and from 31.3% to 60.7% for Kpu.

4. Safety

No serious adverse events were reported. The compound was well tolerated at the doses and dose regimens tested.

5. Summary and Conclusions

After single oral administration of 4-[(7-methoxy-2,3-dihydro-1,4-benzothiazepin-4(5H)yl)methyl]benzoic acid hemifumarate at 20 to 400 mg, $C_{max}$ was reached with median $T_{max}$ values between 3 and 4.5 hrs, after a $t_{lag}$ consistent with the gastro-resistant properties of the tablet (less than 2 hours).

After 14-days of repeated oral administrations of 4-[(7-methoxy-2,3-dihydro-1,4-benzothiazepin-4(5H)yl)methyl]benzoic acid hemifumarate at 20, 60, 120, and 240 mg/d, the $C_{max}$ was reached with a median $T_{max}$ between 3 and 4 hours. Mean apparent terminal half-life was around 20 hrs based on the results of the single and repeat dose studies. No evidence of non-linearity with the time and dose was observed. Overall, inter-individual variability on $C_{max}$ and AUC24 was low at 20, 60, 120, and 240 mg/d. Steady-state was attained after 5 to 7 days of daily treatment. After 14-day repeated administrations of 20, 60, 120, and 240 mg/d of 4-[(7-methoxy-2,3-dihydro-1,4-benzothiazepin-4(5H)yl)methyl]benzoic acid hemifumarate, accumulation ratios were around 1.4-1.8 for $C_{max}$ and $AUC_{24}$, consistent with the half-life of Compound I and the dose regimen. $K_p$ and $K_{pu}$ results are concordant within the dose range (20-240 mg) with [0.04-0.08] and [0.008-0.01] values, respectively.

4-[(7-methoxy-2,3-dihydro-1,4-benzothiazepin-4(5H)yl)methyl]benzoic acid hemifumarate was well tolerated at the doses and dose regimens tested.

Example 7: Clinical Trial in RYR1-Related Myopathy Patients

A Phase 1b study is performed in RYR1-Related Myopathy (RYR1-RM) affected individuals.

Study Objectives

The primary objective is to determine safety and tolerability of Compound I in RYR1-RM affected individuals.

The secondary objectives are: (1) to determine pharmacokinetics of a 28-day administration of Compound I in RYR1-RM affected individuals; (2) to explore whether Compound I increases RyR1-Calstabin1 binding in skeletal muscle of RYR1-RM affected individuals; and (3) to explore whether treatment with Compound I improves muscle function, motor activity, and fatigue in RYR1-RM affected individuals.

Materials and Methods

1. Study Drug

Compound I was administered in a gastro-resistant tablet according to Example 3 at daily doses. The formulation comprised 20 mg Compound I (based on the mass of 4-[(7-methoxy-2,3-dihydro-1,4-benzothiazepin-4(5H)yl)methyl]benzoic acid). The first three participants were dosed with 120 mg of Compound I (6×20 mg tablets) daily for approximately 28 days. The second group was dosed with 200 mg of Compound I (10×20 mg tablets daily for approximately 28 days.

2. Study Design

2a. Pharmacokinetic Measurements

Bloods for PK assessments were at baseline (Day 0, 24 h PK), at the study mid-point (day 14±2 days, trough PK), and at the final study visit (day 28, 24 h PK). Pharmacokinetic analysis was performed on plasma samples. PK parameters are set forth below:

Day 1

| | |
|---|---|
| $AUC_{0-24}$ | The area under the concentration-time curve, from time 0 to the 24 hours post dose, as calculated by the linear trapezoidal method. |
| $AUC_{0-t}$ | The area under the concentration-time curve, from time 0 to the last observed non-zeo concentration, as calculated by the linear trapezoidal method. |
| $AUC_{0-inf}$ | The area under the concentration-time curve from time 0 extrapolated to infinity. AUC0-inf is calculated as the sum of AUC0-t plus the ratio of the last measureable plasma concentration to the elimination rate constant. |
| $AUC\ \%_{extrap}$ | Percent of AUC0-inf extrapolated, represented as (1 − AUC0-t/AUC0-inf)*100. |
| $C_{max}$ | Mazimum observed concentration. |
| $T_{max}$ | Time to reach Cmax. If the maximum value occurs at more than one time point, Tmax is defined as the first time point with this value. |
| Kel | Apparent first-order terminal elimanation rate constant calculated from a semi-log plot of the plasma concentration versus time curve. The parameter will be calculated by linear least-squares regression analysis using the maximum number of points in the terminal log-linear phase (e.g., three or more non-zero plasma concentrations). |
| $t^{1}\!/_{2}$: | Apparent first-order terminal elimanation half-life will be calculated as 0.693/Kel. |
| $T_{lag}$ | Lag time - the time delay between drug administration and the onset of absorption; where onset of absorption can be defined as: the time point prior to the first observed/measured non-zero plasma concentration. |

Day 28

| | |
|---|---|
| $AUC_{tau}$ | The area under the concentaration-time curve during a dosing interval (tau) at steady state. |
| $C_{max}$ | Maximum observed concentration. |
| $T_{max}$ | Time to reach Cmax. If the maximum value occurs at more than one time point, Tmax is defined as the first time point with this value. |
| $C_{min}$ | Minimum observed concentration. |
| $T_{min}$ | Time to reach $C_{min}$. |
| $RA_{AUC}$ | The ratio of accumulation of AUC calculated as the ratio of the $AUC_{tau}$ Day 28/$AUC_{0-24}$ Day 1. |
| $RAC_{max}$ | The ratio of accumulation of Cmax calculated as the ratio of the Cmax Day 28/$C_{max}$ Day 1. |

2b. Muscle Biopsy

Skeletal muscle tissue is obtained from participants pre- and post-intervention by needle biopsy. This tissue is assessed for RyR1-Calstabin1 binding by co-immunoprecipitation followed by protein detection. The percentage of Calstabin1 binding to RyR1 pre-dose is compared to the percentage obtained post-dose in each patient (arbitrary units; AU). Changes from baseline in calcium permeability (Fluo-4 signal) using a thapsigargin assay (AU) are also ascertainable from muscle membrane preparations.

2c. RyR1-Calstabin Binding Assay

Participants undergo two needle muscle biopsies during the study to determine Compound I pharmacodynamics (PD) in the RYR1-RM population. Biopsy 1 is performed pre-dose during study visit 1 (Day −1/Day 1). Biopsy 2 is performed post-dose (Day 27/28). Muscle biopsies are performed on the tibialis anterior or another suitable muscle (i.e. with minimal fatty infiltration). The comparison of pre- and post-treatment muscle tissue assesses whether enough study drug reaches the muscle in either dose level to engage the RyR1 target.

Participant's skeletal muscle tissue is analyzed for RyR1-Calstabin1 association. The assay comprises evaluating the change in the percentage of Calstabin1 binding pre-dose compared to the percentage obtained post-dose. Percent RyR1-Calstabin1 binding is expressed as a percentage of the normal control muscle as determined by RyR1-Calstabin1 co-immunoprecipitation and quantification of RyR1 and Calstabin1.

2d. Calcium Leak Assay

Percent (%) $Ca^{2+}$ leak from RyR1 is measured using a thapsigargin calcium leak assay, a plate reader assay which uses fluorescence produced by a $Ca^{2+}$ indicator to visualize and quantify $Ca^{2+}$ leak from isolated microsomal vesicles containing RyR1 after pharmacologic inhibition of SERCA in vitro by thapsigargin to inhibit the re-uptake pump. Results are shown in change from baseline in relative Fluo-4 signal (AU).

Remaining muscle tissue is used for single channel measurements or derivation of myotubes in cell culture.

2e. Functional Measurements

The following endpoints are measured: Grip strength (kg), pinch strength (kg), quantitative muscle strength assessment (kg), time taken to complete each of the following (seconds): walk 10-meters, supine to stand, ascend 4 stairs, and descend 4 stairs, MFM-32 score for domains 1, 2, 3, and total (% of maximum score), PROMIS-fatigue subscale score (t-score).

Grip and pinch strength: Participants are seated with the elbow flexed to 90 degrees, with the forearm and wrist in neutral position. Participants are then asked to squeeze the dynamometer and pinch the gauge. This process is repeated three times with the best effort used for final analyses.

Quantitative muscle strength assessment: Participants undergo assessment of muscle strength in standardized seated and supine positions. Participants are asked to exert force against an elastic strap-based force transducer.

Graded Functional Tests: Graded functional tests are completed by participants pre- and post-intervention. Participants complete a timed 10-meter walk test, supine to stand, ascend 4 stairs, and descend 4 stairs. The recorded time is listed by subject and summarized descriptively for each test to compare between pre- and post-treatment results.

Results

1. Pharmacokinetics

1a. Pharmacokinetics—120 mg Daily Dose

Pharmacokinetic Parameters of three subjects following a single oral administration of 120 mg Compound I (based on the mass of 4-[(7-methoxy-2,3-dihydro-1,4-benzothiazepin-4(5H)yl)methyl]benzoic acid) on Day 1 are shown in Table 10.

TABLE 10

Single Oral Administration

| Parameter | AUC0-24 (h * ug/mL) | AUC0-t (h * ug/mL) | AUC0-inf (h * ug/mL) | AUC % extrap (%) | Cmax (ug/mL) | Tmax (h) | Kel (l/h) | t1/2 (h) | Tlag (h) |
|---|---|---|---|---|---|---|---|---|---|
| Arithmetic Mean | 171.6 | 171.6 | 258.9 | 33.36 | 13.27 | 3.000 | 0.04929 | 14.142 | 0.167 |
| SD | 20.335 | 20.335 | 41.024 | 3.609 | 2.7062 | 0.0000 | 0.0046064 | 1.2830 | 0.2887 |
| CV % | 11.8 | 11.8 | 15.8 | 10.8 | 20.4 | 0.0 | 9.3 | 9.1 | 173.2 |
| SEM | 11.74 | 11.74 | 23.685 | 2.0836 | 1.5624 | 0.0000 | 0.0026595 | 0.7408 | 0.1667 |
| Min | 150 | 150 | 212 | 29.4 | 11.1 | 3.00 | 0.0454 | 12.75 | 0.00 |
| Median | 174.6 | 174.6 | 274.4 | 34.33 | 12.4 | 3.000 | 0.04813 | 14.401 | 0.000 |
| Max | 190 | 190 | 290 | 36.4 | 16.3 | 3.00 | 0.0544 | 15.28 | 0.50 |
| Geometric Mean | 170.8 | 170.8 | 256.6 | 33.23 | 13.09 | 3.000 | 0.04915 | 14.103 | |
| Geometric CV % | 12.1 | 12.1 | 16.7 | 11.1 | 20 | 0.0 | 9.2 | 9.2 | |

MFM-32: The MFM-32 scale is a validated measure of motor function, and provides a measurement of the effects of muscle weakness in neuromuscular diseases (NMD). Assessments are based on posture and movements of the whole body. The test is administered pre- and post-intervention. The participant is asked to roll, sit, lift head from prone and supine position, get up from a lying position, prop on arms, kneel, crawl, stand, and step. This test is combined with timed tests (e.g., floor to stand, ascend/descend 4 steps). Day 1 versus Day 28 motor function is documented and listed for each subject quantitatively (% of maximum score) using the scoring of the MFM32 for the following: total score, domain 1 (standing and transfers), domain 2 (axial and proximal motor function), and domain 3 (distal motor function). The resulting scores are summarized descriptively to compare between pre- and post-treatments results.

As shown in Table 10, geometric mean $C_{max}$ was approximately 13.1 μg/mL with individual values varying from 11.1 to 16.3 μg/mL. $T_{max}$ was 3 hours for all participants. Geometric mean $AUC_{0-t}$ and $AUC_{0-inf}$ were 171 and 257 h*μg/mL with individual values varying from 150 to 190 and 212 to 290 h*μg/mL, respectively. Mean half-life of Compound I was 14.14 hours, with individual values of 14.40, 12.75, and 15.28 hours.

Figure 6:
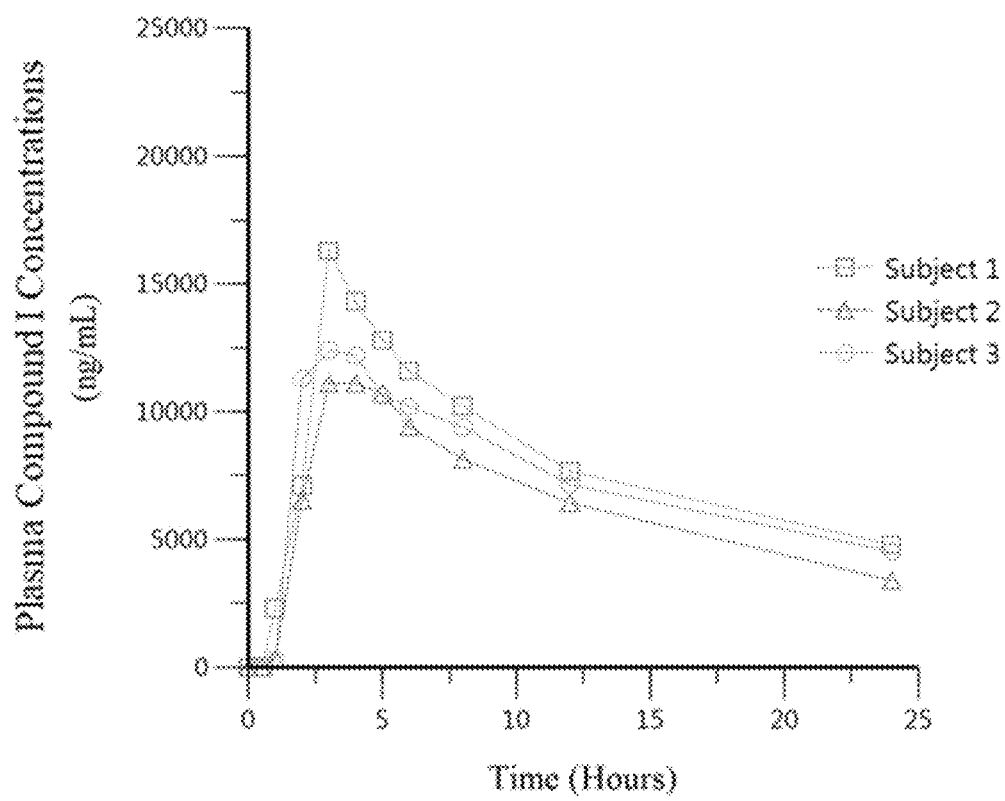
FIG. 6: Individual plasma concentration time profile of Compound I on Day 1 after a single oral dose administration of 120 mg Compound I, formulated in gastro-resistant tablets (6 tablets per dose) to three RYR1-Related Myopathy patients.

Individual plasma concentration of Compound I after single dose of 120 mg Compound I on Day 1 are presented in FIG. 6.

Pharmacokinetic Parameters Following multiple oral daily doses of 120 mg Compound I for 28 days are shown in Table 11.

TABLE 11

28 Days Multiple Oral Administrations

| Parameter | AUC0-tau (h * ug/mL) | Cmax,ss (ug/mL) | Tmax,ss (h) | Cmin (ug/mL) | Tmin (h) | RA_AUC | RA_Cmax | Ctrough_D13 (ug/mL) |
|---|---|---|---|---|---|---|---|---|
| n | 3 | 3 | 3 | 3 | 3 | 3 | 3 | 3 |
| Arithmetic Mean | 271.6 | 19.33 | 4.667 | 6.860 | 16.333 | 1.587 | 1.485 | 8.050 |
| SD | 25.106 | 2.2368 | 1.1547 | 0.98975 | 13.2791 | 0.07650 | 0.25360 | 1.3450 |
| CV % | 9.2 | 11.6 | 24.7 | 14.4 | 81.3 | 4.8 | 17.1 | 16.7 |
| SEM | 14.495 | 1.2914 | 0.6667 | 0.57143 | 7.6667 | 0.04410 | 0.14640 | 0.77655 |
| Min | 243 | 16.9 | 4.00 | 5.80 | 1.00 | 1.50 | 1.21 | 6.71 |
| Median | 285.4 | 19.8 | 4.000 | 7.020 | 24.000 | 1.618 | 1.523 | 8.040 |
| Max | 287 | 21.3 | 6.00 | 7.76 | 24.00 | 1.64 | 1.72 | 9.40 |
| Geometric Mean | 270.8 | 19.24 | 4.579 | 6.811 | 8.320 | 1.585 | 1.470 | 7.974 |
| Geometric CV % | 9.5 | 11.9 | 23.7 | 14.9 | 529.0 | 4.9 | 17.7 | 17.0 |

Fatigue Questionnaire: The validated PROMIS-fatigue subscale is administered. Participants are asked to enter responses for fatigue-related quality of life questions pre- and post-intervention.

2f. Safety and Tolerability

Safety and tolerability of Compound I is determined by monitoring Adverse Events (AEs) over approximately 28 days of treatment via patient interviews, patient diary reviews, physical examinations, echocardiograms, electrocardiograms (ECGs), vital signs, and laboratory safety tests.

Geometric mean $C_{max,ss}$ was approximately 19.2 μg/mL with individual values varying from 16.9 to 21.3 μg/mL. $T_{max,ss}$ was 4 hours post dose for two participants and 6 hours post dose for the third subject. Geometric mean $AUC_{0-tau}$ was approximately 271 h*μg/mL with individual values varying from 243 to 287 h*μg/mL, respectively. $C_{min}$ varied from 5.80 to 7.76 μg/mL and occurred at 1 hour post-dose for 1 subject and at 24 hours post-dose for two subjects. Geometric mean Day 13 $C_{trough}$ was 7.97 μg/mL with individual $C_{trough}$ values varying from 6.71 to 9.40

µg/mL. Geometric mean (geometric CV %) accumulation ratio for AUC and $C_{max}$ was 1.59 (4.9) and 1.47 (17.7), respectively.

Figure 7:
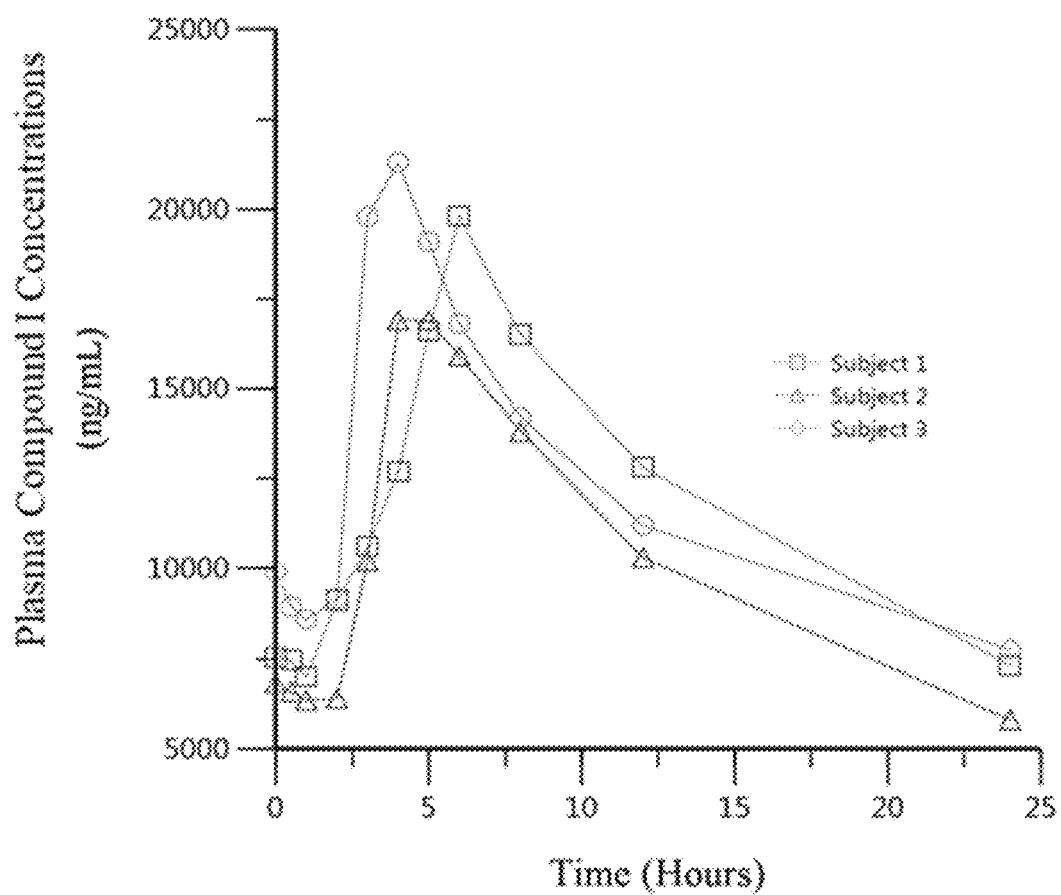
FIG. 7: Individual plasma concentration time profile of Compound I on Day 28 after multiple oral daily doses of 120 mg Compound I, formulated in gastro-resistant tablets (6 tablets per dose) to three RYR1-Related Myopathy patients.

Individual plasma concentrations of Compound I after multiple daily doses of 120 mg Compound I on Day 28 are presented in FIG. 7.

1b. Pharmacokinetics—200 mg Daily Dose

Figure 8:
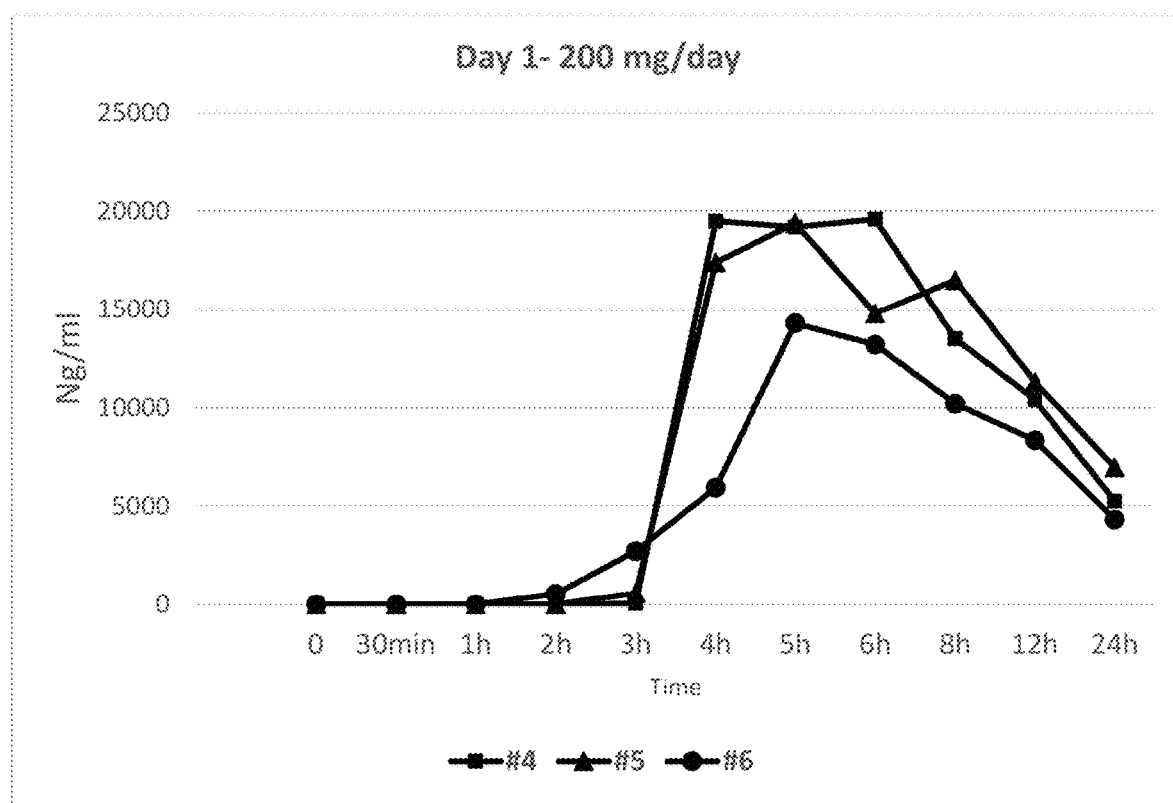
FIG. 8: Individual plasma concentration time profile of Compound I on Day 1 after a single oral dose administration of 200 mg Compound I, formulated in gastro-resistant tablets (10 tablets per dose) to three RYR1-Related Myopathy patients.

Mean plasma concentrations from three subjects following a single oral administration of 200 mg Compound I (based on the mass of 4-[(7-methoxy-2,3-dihydro-1,4-benzothiazepin-4(5H)yl)methyl]benzoic acid) are shown in Table 12. Individual plasma concentrations are shown in FIG. 8. $T_{max}$ was 5-6 hours for all participants.

TABLE 12

| Single Oral Administration | |
|---|---|
| Time (hr) | Conc. (ng/mL) |
| 0 | 0 |
| 0.5 | 0 |
| 1 | 0 |
| 2 | 176.33 |
| 3 | 1109.9 |
| 4 | 14280.0 |
| 5 | 17633.33 |
| 6 | 15866.67 |
| 8 | 13400.0 |
| 12 | 10013.33 |
| 24 | 5516.61 |

Figure 9:
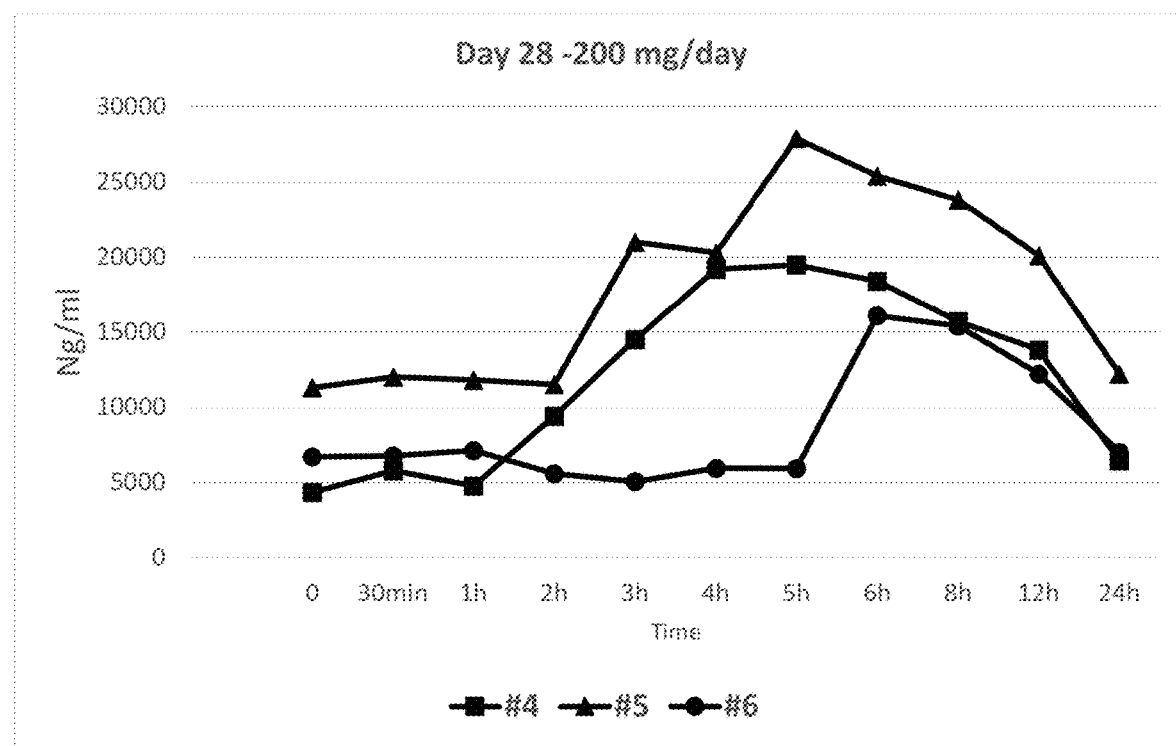
FIG. 9: Individual plasma concentration time profile of Compound I on Day 28 after multiple oral daily doses of 200 mg Compound I, formulated in gastro-resistant tablets (10 tablets per dose), to three RYR1-Related Myopathy patients.

Mean plasma concentrations from three subjects following multiple oral daily doses of 200 mg Compound I (based on the mass of 4-[(7-methoxy-2,3-dihydro-1,4-benzothiazepin-4(5H)yl)methyl]benzoic acid) for 28 days are shown in Table 13. Individual plasma concentrations are shown in FIG. 9. $T_{max}$ was 5-6 hours for all participants.

TABLE 13

| 28 Days Multiple Oral Administrations | |
|---|---|
| Time (hr) | Conc. (ng/mL) |
| 0 | 7450 |
| 0.5 | 8186.67 |
| 1 | 7896.67 |
| 2 | 8826.67 |
| 3 | 13520 |
| 4 | 15146.67 |
| 5 | 17773.33 |
| 6 | 19966.67 |
| 8 | 18300 |
| 12 | 15366.67 |
| 24 | 8553.33 |

RyR1-Calstabin1 binding, calcium leak and functional measurements are each determined.

Example 8: Preparation of 4-[(7-methoxy-2,3-dihydro-1,4-benzothiazepin-4(5H)yl)methyl]benzoic acid 4-[(7-methoxy-2,3-dihydro-1,4-benzothiazepin-4(5H)yl) methyl]benzoic acid was prepared as described below.

Stage 1: 7-methoxy-2,3,4,5-tetrahydrobenzo[f][1,4]thiazepine ("Amine")

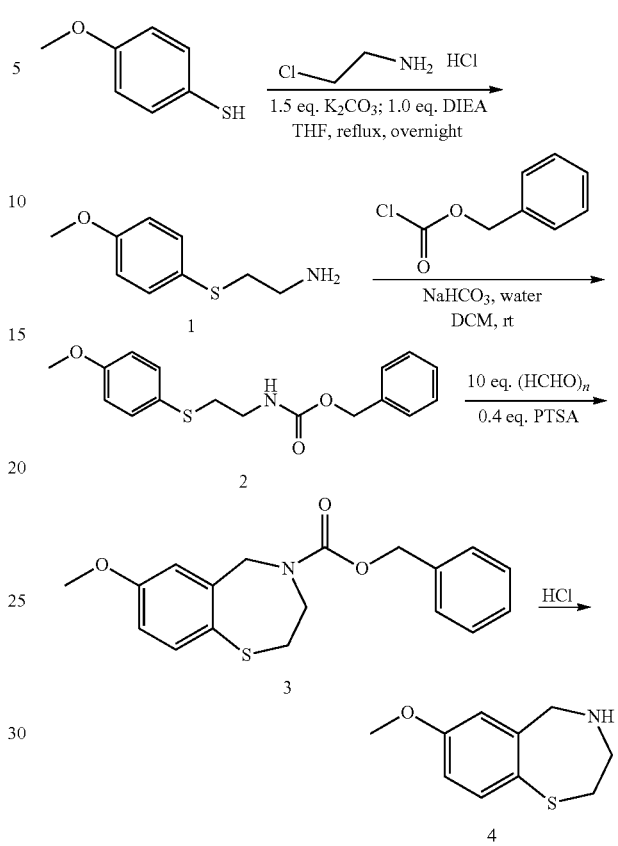

Scheme 1

2-(4-Methoxyphenylthio)ethanamine (1)

4-Methoxythiophenol (50 g, 0.357 mol), 2-chloroethylamine monohydrochloride (39.8 g, 0.343 mol.), $K_2CO_3$ (78.8 g, 0.57 mol), and diisopropyl ethylamine (32 mL, 0.178 mol) were mixed in tetrahydrofuran (THF). The mixture was degassed for 5 min. under reduced pressure and heated at reflux under argon overnight. The solvent was removed and water was added to the flask. The mixture was extracted with dichloromethane. The organic layers were collected, dichloromethane was removed and conc. HCl was added, followed by of water. The solution was extracted with 1:1 ethyl acetate (EtOAc)/hexane. The aqueous layer was adjusted to pH 10 with 2 M NaOH, and was extracted with dichloromethane. The combined organic solution was dried over anhydrous sodium sulfate. Removal of solvent provided the target compound.

Benzyl 2-(4-methoxyphenylthio)ethylcarbamate (2)

To a flask containing Compound I (8.0 g, 43.7 mmol), sodium bicarbonate (12.1 g, 144 mmol), water, and dichloromethane was added benzyl chloroformate (8.2 g, 48.1 mmol, diluted in 100 mL of dichloromethane) dropwise at 0° C. After the addition, the mixture was stirred at room temperature (r.t.) for 5 hr. The organic layer was collected and the aqueous solution was extracted with 100 mL of dichloromethane. The combined organic solution was dried over sodium sulfate. The solvent was removed and the resulting solid was triturated with THF/hexane (1:10). The solid was collected and dried leaving the target product.

Benzyl 7-methoxy-2,3-dihydrobenzo[f][1,4]thiazepine-4(5H)-carboxylate (3)

A mixture of compound 2 (7.3 g, 23 mmol), paraformaldehyde (6.9 g 0.23 mol), and p-toluenesulfonic acid (1.45 g, 7.6 mmol) in toluene was stirred at 70° C. overnight. After cooling to r.t., the solid was filtered off. The solution was extracted with saturated sodium carbonate, and the organic layer was dried over anhydrous sodium sulfate to yield the target product as a liquid after removal of the solvent.

7-Methoxy-2,3,4,5-tetrahydrobenzo[f][1,4]thiazepine hydrobromide (Amine)

Compound 3 (10 g, 30 mmol) was mixed with conc. HCl, water and dioxane. The mixture was stirred at 100° C. overnight. After cooling to r.t., most of the solvent and HCl were removed under reduced pressure. Water was added to the solution and the solid was filtered off. The aqueous solution was extracted with EtOAc/hexane (1:1) and basified by adding 15 g of NaOH. The mixture was extracted with dichloromethane. The combined solution was dried over anhydrous sodium sulfate. Removal of solvent provided a liquid that solidified after standing at r.t., to yield the target compound.

Stage 2: –[(7-methoxy-2,3-dihydro-1,4-benzothiazepin-4(5H)yl)methyl]benzoic acid

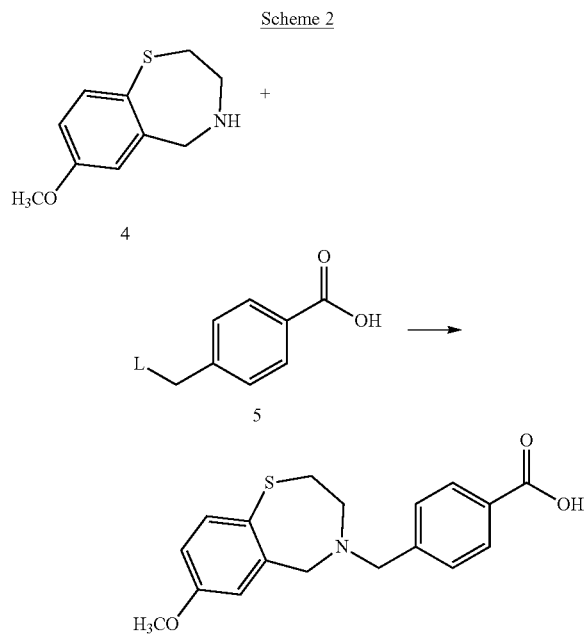

In Scheme 2, L is a leaving group, which is, by way of example, a halogen or a sulfonate (OSO$_2$R' wherein R' is alkyl or aryl, e.g., OMs (mesylate), OTs (tosylate)). Amine (4) (1 mmol) was dissolved dichloromethane. To the solution was added alkylation reagent (5) (1 mmol), followed by N,N-diisopropylethylamine (2 mmol). The mixture was stirred at r.t. overnight. The solution was loaded onto a silica gel column directly and eluted with hexane/EtOAc (2:1, v/v) to afford the desired product.

Preparation of 4-[(7-methoxy-2,3-dihydro-1,4-benzothiazepin-4(5H)yl)methyl]benzoic acid hemifumarate—Form 1

4-[(7-methoxy-2,3-dihydro-1,4-benzothiazepin-4(5H)yl)methyl]benzoic acid was prepared as in Example 1. To form the hemifumarate salt, 4-[(7-methoxy-2,3-dihydro-1,4-benzothiazepin-4(5H)yl)methyl]benzoic acid was salified with fumaric acid in the presence of isopropanol, as depicted in Scheme 3. After cooling, the obtained product was filtered and washed with isopropanol to give the title product.

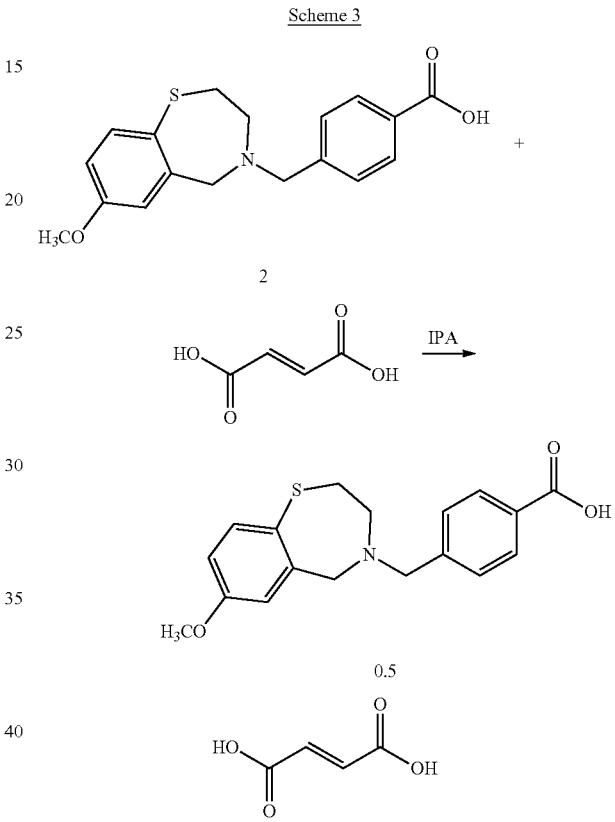

Form 1 can optionally be ground to a particle size distribution described in Table 12.

TABLE 12

| . Particle size | |
| --- | --- |
| D(v, 0.1) | 3.4 µm ≤ D(v, 0.1) ≤ 4.4 µm |
| –D(v, 0.5) | 6.9 µm ≤ D(v, 0.5) ≤ 9.75 µm |
| –D(v, 0.9) | 13.4 µm ≤ D(v, 0.9) ≤ 19.5 µm |

Preparation of 4-[(7-methoxy-2,3-dihydro-1,4-benzothiazepin-4(5H)yl)methyl]benzoic acid hemifumarate—Form 2

4-[(7-methoxy-2,3-dihydro-1,4-benzothiazepin-4(5H)yl)methyl]benzoic acid was prepared as in Example 1. To form the hemifumarate salt, 4-[(7-methoxy-2,3-dihydro-1,4-benzothiazepin-4(5H)yl)methyl]benzoic acid was salified with fumaric acid in the presence of a mixture of dimethylsulfoxide and water, as depicted in Scheme 4. After cooling, the obtained product was filtered and washed with water and acetone to give the desired product.

Scheme 4

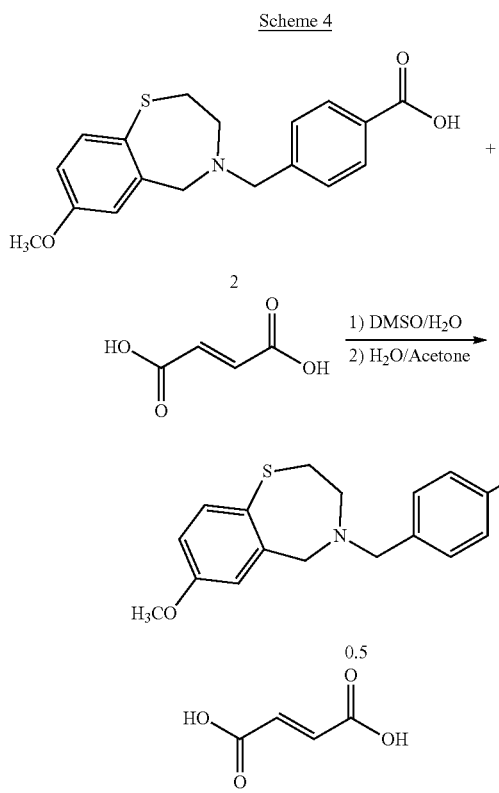

Form 2 can optionally be ground to a particle size distribution described in Table 13.

TABLE 13

| . Particle size | |
|---|---|
| −D(v, 0.5) | 10 μm ≤ D(v, 0.5) ≤ 30 μm |
| −D(v, 0.9) | ≤90 μm |

INCORPORATION BY REFERENCE

All publications, patents, and patent applications mentioned in this specification are herein incorporated by reference to the same extent as if each individual publication, patent, or patent application was specifically and individually indicated to be incorporated by reference.

EMBODIMENTS

Embodiment 1. A pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

Embodiment 2. The pharmaceutical composition of embodiment 1, comprising the pharmaceutically-acceptable salt, wherein the pharmaceutically-acceptable salt is a hemifumarate salt.

Embodiment 3. The pharmaceutical composition of embodiment 1 or 2, wherein the prolonged release is modified release.

Embodiment 4. The pharmaceutical composition of embodiment 1 or 2, wherein the prolonged release is extended release.

Embodiment 5. The pharmaceutical composition of embodiment 1 or 2, wherein the prolonged release is delayed release.

Embodiment 6. The pharmaceutical composition of any one of embodiments 1-5, wherein the unit dosage form is suitable for oral administration.

Embodiment 7. The pharmaceutical composition of any one of embodiments 1-6, wherein the unit dosage form is a solid dosage form.

Embodiment 8. The pharmaceutical composition of any one of embodiments 1-7, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 12 hours.

Embodiment 9. The pharmaceutical composition of any one of embodiments 1-7, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 24 hours.

Embodiment 10. The pharmaceutical composition of any one of embodiments 1-7, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 6 hours after administration.

Embodiment 11. The pharmaceutical composition of any one of embodiments 1-7, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 2 to about 4 hours after administration.

Embodiment 12. The pharmaceutical composition of any one of embodiments 1-7, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at about 3 to about 4 hours after administration.

Embodiment 13. The pharmaceutical composition of any one of embodiments 1-7, wherein in a controlled study, if the unit dosage form is administered to a study subject, then an in-vivo half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof of about 14 to about 21 hours is obtained in the subject.

Embodiment 14. The pharmaceutical composition of embodiment 12, wherein the half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is about 14 hours.

Embodiment 15. The pharmaceutical composition of embodiment 13, wherein the half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is about 20 hours.

Embodiment 16. The pharmaceutical composition of any one of embodiments 1-7, wherein in a controlled study, if the unit dosage form is administered to a study subject, then an accumulation ratio for $C_{max}$ of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio is calculated as a ratio of $C_{max}$ on Day 28/$C_{max}$ on Day 1, wherein $C_{max}$ is maximum observed plasma concentration.

Embodiment 17. The pharmaceutical composition of any one of embodiments 1-7, wherein in a controlled study, if the unit dosage form is administered to a study subject, then an accumulation ratio for AUC of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio for AUC is calculated as a ratio of $AUC_{tau}$ on Day 28/$AUC_{0-24}$ Day 1,
wherein
AUC is area under the concentration-time curve;
$AUC_{tau}$ is area under the concentration-time curve during a dosing interval (tau) at steady-state; and
$AUC_{0-24}$ is area under the concentration-time curve, from time 0 to 24 hours post-dose.

Embodiment 18. The pharmaceutical composition of any one of embodiments 1-7, wherein in a controlled study, if the unit dosage form is administered to a study subject, then a maximum observed plasma concentration of less than about 35 ug/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject.

Embodiment 19. The pharmaceutical composition of any one of embodiments 1-7, wherein in a controlled study, if the unit dosage form is administered to a study subject, then a maximum observed plasma concentration of about 10 to about 15 ng/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject after a single administration of a 120 mg dose.

Embodiment 20. The pharmaceutical composition of any one of embodiments 1-7, wherein in a controlled study, if the unit dosage form is administered to a study subject, then a maximum observed plasma concentration of about 17 to about 21 ng/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject after 14 once-daily administrations of a 120 mg dose.

Embodiment 21. The pharmaceutical composition of any one of embodiments 1-7, wherein in a controlled study, if the unit dosage form is administered to a study subject, then a steady-state plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof occurs in the study subject in a range of about 3 to about 7 days after initial administration.

Embodiment 22. The pharmaceutical composition of any one of embodiments 1-21, comprising about 20 to about 200 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 23. The pharmaceutical composition of any one of embodiments 1-21, comprising about 23.5 to about 235 mg of 4-[(7-methoxy-2,3-dihydro-1,4-benzothiazepin-4(5H)yl)methyl]benzoic acid hemifumarate.

Embodiment 24. The pharmaceutical composition of any one of embodiments 1-23, comprising 20 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 25. The pharmaceutical composition of any one of embodiments 1-23, comprising 23.5 mg of 4-[(7-methoxy-2,3-dihydro-1,4-benzothiazepin-4(5H)yl)methyl]benzoic acid hemifumarate.

Embodiment 26. The pharmaceutical composition of any one of embodiments 1-23, comprising 50 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 27. The pharmaceutical composition of any one of embodiments 1-23, comprising 58.75 mg of 4-[(7-methoxy-2,3-dihydro-1,4-benzothiazepin-4(5H)yl)methyl]benzoic acid hemifumarate.

Embodiment 28. The pharmaceutical composition of any one of embodiments 1-23, comprising 100 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 29. The pharmaceutical composition of any one of embodiments 1-23, comprising 117.5 mg of 4-[(7-methoxy-2,3-dihydro-1,4-benzothiazepin-4(5H)yl)methyl]benzoic acid hemifumarate.

Embodiment 30. The pharmaceutical composition of any one of embodiments 1-29, wherein the unit dosage form is a tablet.

Embodiment 31. The pharmaceutical composition of any one of embodiments 1-29, wherein the unit dosage form is a tablet, wherein the tablet is prepared by a wet granulation process.

Embodiment 32. The pharmaceutical composition of any one of embodiments 1-29, wherein the unit dosage form is a tablet, wherein the tablet is prepared by a dry granulation process.

Embodiment 33. The pharmaceutical composition of any one of embodiments 1-32, wherein the unit dosage form is a gastro-resistant tablet.

Embodiment 34. The pharmaceutical composition of embodiment 33, wherein the gastro-resistant tablet does not substantially disintegrate at a pH at or below 5.5, wherein disintegration is determined by measuring dissolution of the gastro-resistant tablet in a medium having a pH at or below 5.5.

Embodiment 35. The pharmaceutical composition of embodiment 34, wherein the medium having a pH at or below 5.5 is 0.1N HCl solution having a pH of 1.2.

Embodiment 36. The pharmaceutical composition of embodiment 33, wherein the gastro-resistant tablet substantially disintegrates at a pH of at least about 6.8, wherein disintegration is determined by measuring dissolution of the gastro-resistant tablet in a medium having a pH of 6.8.

Embodiment 37. The pharmaceutical composition of embodiment 36, wherein the medium having a pH of 6.8 is a phosphate buffer.

Embodiment 38. The pharmaceutical composition of embodiment 33, wherein gastro-resistant tablet does not substantially disintegrate in gastric fluid.

Embodiment 39. The pharmaceutical composition of embodiment 33, wherein the gastro-resistant tablet substantially disintegrates in intestinal fluid.

Embodiment 40. The pharmaceutical composition of any one of embodiments 1-39, wherein the unit dosage form is a gastro-resistant tablet, wherein the gastro-resistant tablet comprises a core and a coating layer substantially covering the core.

Embodiment 41. The pharmaceutical composition of embodiment 40, wherein the coating layer comprises an enteric polymer.

Embodiment 42. The pharmaceutical composition of embodiment 41, wherein the enteric polymer is hypromellose acetate succinate.

Embodiment 43. The pharmaceutical composition of embodiment 40, wherein the coating layer is about 20% by mass of the tablet.

Embodiment 44. The pharmaceutical composition of embodiment 40, further comprising a sub-coating layer between the core and the coating layer.

Embodiment 45. The pharmaceutical composition of embodiment 44, wherein the sub-coating layer comprises a polymer.

Embodiment 46. The pharmaceutical composition of embodiment 45, wherein the polymer is hypromellose.

Embodiment 47. The pharmaceutical composition of any one of embodiments 44-46, wherein the sub-coating layer is about 3% by mass of the tablet.

Embodiment 48. The pharmaceutical composition of any one of embodiments 1-47, wherein the pharmaceutically-acceptable excipient is a binder.

Embodiment 49. The pharmaceutical composition of any one of embodiments 1-47, wherein the pharmaceutically-acceptable excipient is a diluent.

Embodiment 50. The pharmaceutical composition of any one of embodiments 1-47, wherein the pharmaceutically-acceptable excipient is a disintegrant.

Embodiment 51. The pharmaceutical composition of any one of embodiments 1-47, wherein the pharmaceutically-acceptable excipient is a glidant.

Embodiment 52. The pharmaceutical composition of any one of embodiments 1-47, wherein the pharmaceutically-acceptable excipient is a lubricant.

Embodiment 53. The pharmaceutical composition of any one of embodiments 1-47, wherein the pharmaceutically-acceptable excipient is a surfactant.

Embodiment 54. The pharmaceutical composition of any one of embodiments 1-47, wherein the pharmaceutically-acceptable excipient is mannitol.

Embodiment 55. The pharmaceutical composition of embodiment 54, wherein the mannitol is present at about 5% to about 15% by mass of the composition.

Embodiment 56. The pharmaceutical composition of any one of embodiments 1-47, wherein the pharmaceutically-acceptable excipient is microcrystalline cellulose.

Embodiment 57. The pharmaceutical composition of embodiment 56, wherein the microcrystalline cellulose is present at about 10% to about 20% by mass of the composition.

Embodiment 58. The pharmaceutical composition of any one of embodiments 1-47, wherein the pharmaceutically-acceptable excipient is croscarmellose sodium.

Embodiment 59. The pharmaceutical composition of embodiment 58, wherein the croscarmellose sodium is present at about 1% to about 5% by mass of the composition.

Embodiment 60. The pharmaceutical composition of any one of embodiments 1-47, wherein the pharmaceutically-acceptable excipient is magnesium stearate.

Embodiment 61. The pharmaceutical composition of embodiment 60, wherein the magnesium stearate is present at about 0.5% to about 2% by mass of the composition.

Embodiment 62. The pharmaceutical composition of any one of embodiments 1-47, wherein the pharmaceutically-acceptable excipient is maltodextrin.

Embodiment 63. The pharmaceutical composition of embodiment 62, wherein the maltodextrin is present at about 5% to about 15% by mass of the composition.

Embodiment 64. The pharmaceutical composition of any one of embodiments 1-47, wherein the pharmaceutically-acceptable excipient is colloidal anhydrous silica.

Embodiment 65. The pharmaceutical composition of embodiment 64, wherein the colloidal anhydrous silica is present at about 0.1% to about 0.5% by mass of the composition.

Embodiment 66. The pharmaceutical composition of any one of embodiments 1-47, wherein the pharmaceutically-acceptable excipient is sodium stearyl fumarate.

Embodiment 67. The pharmaceutical composition of embodiment 66, wherein the sodium stearyl fumarate is present at about 0.5% to about 1% by mass of the composition.

Embodiment 68. The pharmaceutical composition of any one of embodiments 1-47, wherein the pharmaceutically-acceptable excipient is hypromellose.

Embodiment 69. The pharmaceutical composition of embodiment 68, wherein the hypromellose is present at about 1% to about 5% by mass of the composition.

Embodiment 70. The pharmaceutical composition of any one of embodiments 1-47, wherein the pharmaceutically-acceptable excipient is stearic acid.

Embodiment 71. The pharmaceutical composition of embodiment 70, wherein the stearic acid is present at about 0.1% to about 0.5% by mass of the composition.

Embodiment 72. The pharmaceutical composition of any one of embodiments 1-47, wherein the pharmaceutically-acceptable excipient is hypromellose acetate succinate.

Embodiment 73. The pharmaceutical composition of embodiment 72, wherein the hypromellose acetate succinate is present at about 5% to about 15% by mass of the composition.

Embodiment 74. The pharmaceutical composition of any one of embodiments 1-47, wherein the pharmaceutically-acceptable excipient is triethyl citrate.

Embodiment 75. The pharmaceutical composition of embodiment 74, wherein the triethyl citrate is present at about 1% to about 5% by mass of the composition.

Embodiment 76. The pharmaceutical composition of any one of embodiments 1-47, wherein the pharmaceutically-acceptable excipient is sodium lauryl sulfate.

Embodiment 77. The pharmaceutical composition of embodiment 76, wherein the sodium lauryl sulfate is present at about 0.1% to about 0.5% by mass of the composition.

Embodiment 78. The pharmaceutical composition of any one of embodiments 1-47, wherein the pharmaceutically-acceptable excipient is talc.

Embodiment 79. The pharmaceutical composition of embodiment 78, wherein the talc is present at about 1% to about 5% by mass of the composition.

Embodiment 80. A method of treating a condition, comprising administering to a subject in need thereof a therapeutically-effective amount of a pharmaceutical composition, the pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a prolonged release of 4-[(7-methoxy-2,3-dihydro-1,4-benzothiazepin-4(5H)yl)methyl]benzoic acid or the pharmaceutically-acceptable salt thereof in the subject is attained.

Embodiment 81. The method of embodiment 80, wherein the condition is a cardiac condition.

Embodiment 82. The method of embodiment 81, wherein the cardiac condition is characterized by an irregular heartbeat.

Embodiment 83. The method of embodiment 81 or 82, wherein the cardiac condition is catecholaminergic polymorphic ventricular tachycardia.

Embodiment 84. The method of embodiment 81, wherein the cardiac condition is heart failure.

Embodiment 85. The method of embodiment 84, wherein the heart failure is congestive heart failure.

Embodiment 86. The method of embodiment 84, wherein the heart failure is chronic heart failure.

Embodiment 87. The method of embodiment 84, wherein the heart failure is heart failure with reduced ejection fraction.

Embodiment 88. The method of embodiment 84, wherein the heart failure is heart failure with preserved ejection fraction.

Embodiment 89. The method of any one of embodiments 84-86, wherein the subject is a heart failure patient having an implantable cardioverter-defibrillator, wherein the implantable cardioverter-defibrillator is implanted in the patient.

Embodiment 90. The method of embodiment 84, wherein the heart failure is acute heart failure.

Embodiment 91. The method of embodiment 84, wherein the subject is a heart failure patient in need of preservation of cardiac function post myocardial infarction.

Embodiment 92. The method of embodiment 81, wherein the cardiac condition is myocardial infarction.

Embodiment 93. The method of embodiment 81, wherein the cardiac condition comprises cardiac ischemia/reperfusion injury.

Embodiment 94. The method of embodiment 80, wherein the condition is a musculoskeletal condition.

Embodiment 95. The method of embodiment 94, wherein the musculoskeletal condition is a congenital myopathy.

Embodiment 96. The method of embodiment 95, wherein the congenital myopathy is RYR1-related myopathy.

Embodiment 97. The method of embodiment 94, wherein the musculoskeletal condition is a muscular dystrophy.

Embodiment 98. The method of embodiment 97, wherein the muscular dystrophy is Duchenne Muscular Dystrophy.

Embodiment 99. The method of embodiment 94, wherein the musculoskeletal condition is sarcopenia.

Embodiment 100. The method of embodiment 80, wherein the condition is cancer associated muscle weakness.

Embodiment 101. The method of embodiment 100, wherein the cancer associated muscle weakness is cancer cachexia.

Embodiment 102. The method of embodiment 101, wherein the cancer cachexia is due to a cancer having bone metastases.

Embodiment 103. The method of embodiment 80, wherein the condition is diabetes.

Embodiment 104. The method of embodiment 80, wherein the condition is malignant hyperthermia.

Embodiment 105. The method of any one of embodiments 80-104, wherein the therapeutically-effective amount is about 100 to about 200 mg per day.

Embodiment 106. The method of any one of embodiments 80-105, wherein the therapeutically-effective amount is about 120 mg per day.

Embodiment 107. The method of any one of embodiments 80-105, wherein the therapeutically-effective amount is about 200 mg per day.

Embodiment 108. The method of any one of embodiments 80-107, wherein the administering is oral.

Embodiment 109. The method of any one of embodiments 80-108, wherein the salt is a hemifumarate salt.

Embodiment 110. The method of any one of embodiments 80-109, wherein the prolonged release is modified release.

Embodiment 111. The method of any one of embodiments 80-110, wherein the prolonged release is extended release.

Embodiment 112. The method of any one of embodiments 80-111, wherein the prolonged release is delayed release.

Embodiment 113. The method of any one of embodiments 80-112, wherein the unit dosage form is a solid dosage form.

Embodiment 114. The method of any one of embodiments 80-113, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 12 hours.

Embodiment 115. The method of any one of embodiments 80-113, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 24 hours.

Embodiment 116. The method of any one of embodiments 80-113, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject about 2 to about 6 hours after administration.

Embodiment 117. The method of any one of embodiments 80-113, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject about 2 to about 4 hours after administration.

Embodiment 118. The method of any one of embodiments 80-113, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject about 3 to about 4 hours after administration.

Embodiment 119. The method of any one of embodiments 80-113, wherein in a controlled study, if the unit dosage form is administered to a study subject, then an in-vivo half-life of 4-[(7-methoxy-2,3-dihydro-1,4-benzothiazepin-4(5H)yl) methyl]benzoic acid or the pharmaceutically-acceptable salt thereof or a pharmaceutically-acceptable ion thereof of about 14 to about 21 hours is obtained in the subject.

Embodiment 120. The method of embodiment 119, wherein the half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is about 14 hours.

Embodiment 121. The method of embodiment 119, wherein the half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is about 20 hours.

Embodiment 122. The method of any one of embodiments 80-113, wherein in a controlled study, if the unit dosage form is administered to a study subject, then an accumulation ratio for $C_{max}$ of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio is calculated as a ratio of $C_{max}$ on Day 28/$C_{max}$ on Day 1, wherein $C_{max}$ is maximum observed plasma concentration.

Embodiment 123. The method of any one of embodiments 80-113, wherein in a controlled study, if the unit dosage form is administered to a study subject, then an accumulation ratio for AUC of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio for AUC is calculated as a ratio of $AUC_{tau}$ on Day 28/$AUC_{0-24}$ Day 1,
wherein
AUC is area under the concentration-time curve;
$AUC_{tau}$ is area under the concentration-time curve during a dosing interval (tau) at steady-state; and
$AUC_{0-24}$ is area under the concentration-time curve, from time 0 to 24 hours post-dose.

Embodiment 124. The method of any one of embodiments 80-113, wherein in a controlled study, if the unit dosage form is administered to a study subject, then a maximum observed plasma concentration of less than about 35 ug/mL of 4-[(7-methoxy-2,3-dihydro-1,4-benzothiazepin-4(5H)yl)methyl] benzoic acid or the pharmaceutically-acceptable salt thereof or a pharmaceutically-acceptable ion thereof is present in the subject.

Embodiment 125. The method of any one of embodiments 80-113, wherein in a controlled study, if the unit dosage form is administered to a study subject, then a maximum observed plasma concentration of about 10 to about 15 ng/mL of 4-[(7-methoxy-2,3-dihydro-1,4-benzothiazepin-4(5H)yl) methyl]benzoic acid or the pharmaceutically-acceptable salt thereof or a pharmaceutically-acceptable ion thereof is present in the subject after a single administration of a 120 mg dose.

Embodiment 126. The method of any one of embodiments 80-113, wherein in a controlled study, if the unit dosage form is administered to a study subject, then a maximum observed plasma concentration of about 17 to about 21 ng/mL of 4-[(7-methoxy-2,3-dihydro-1,4-benzothiazepin-4(5H)yl) methyl]benzoic acid or the pharmaceutically-acceptable salt thereof or a pharmaceutically-acceptable ion thereof is present in the subject after 14 once-daily administrations of a 120 mg dose.

Embodiment 127. The method of any one of embodiments 80-113, wherein in a controlled study, if the unit dosage form is administered to a study subject, then a steady-state plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof occurs in the study subject in a range of about 3 to about 7 days after initial administration.

Embodiment 128. The method of any one of embodiments 80-127, wherein the unit dosage form comprises about 20 to about 200 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 129. The method of any one of embodiments 80-127, wherein the unit dosage form comprises about 23.5 to about 235 mg of 4-[(7-methoxy-2,3-dihydro-1,4-benzothiazepin-4(5H)yl)methyl]benzoic acid hemifumarate.

Embodiment 130. The method of any one of embodiments 80-127, wherein the unit dosage form comprises 20 mg of 4-[(7-methoxy-2,3-dihydro-1,4-benzothiazepin-4(5H)yl) methyl]benzoic acid hemifumarate, based on mass of 4-[(7-methoxy-2,3-dihydro-1,4-benzothiazepin-4(5H)yl)methyl] benzoic acid.

Embodiment 131. The method of any one of embodiments 80-127, wherein the unit dosage form comprises 23.5 mg of 4-[(7-methoxy-2,3-dihydro-1,4-benzothiazepin-4(5H)yl) methyl]benzoic acid hemifumarate.

Embodiment 132. The method of any one of embodiments 80-127, wherein the unit dosage form comprises 50 mg of 4-[(7-methoxy-2,3-dihydro-1,4-benzothiazepin-4(5H)yl) methyl]benzoic acid hemifumarate, based on mass of 4-[(7-methoxy-2,3-dihydro-1,4-benzothiazepin-4(5H)yl)methyl] benzoic acid.

Embodiment 133. The method of any one of embodiments 80-127, wherein the unit dosage form comprises 58.75 mg of 4-[(7-methoxy-2,3-dihydro-1,4-benzothiazepin-4(5H)yl) methyl]benzoic acid hemifumarate.

Embodiment 134. The method of any one of embodiments 80-127, wherein the unit dosage form comprises 100 mg of 4-[(7-methoxy-2,3-dihydro-1,4-benzothiazepin-4(5H)yl) methyl]benzoic acid hemifumarate, based on mass of 4-[(7-methoxy-2,3-dihydro-1,4-benzothiazepin-4(5H)yl)methyl] benzoic acid.

Embodiment 135. The method of any one of embodiments 80-127, wherein the unit dosage form comprises 117.5 mg of 4-[(7-methoxy-2,3-dihydro-1,4-benzothiazepin-4(5H)yl) methyl]benzoic acid hemifumarate.

Embodiment 136. The method of any one of embodiments 80-135, wherein the unit dosage form is a tablet.

Embodiment 137. The method of any one of embodiments 80-135, wherein the unit dosage form is a tablet, wherein the tablet is prepared by a wet granulation process.

Embodiment 138. The method of any one of embodiments 80-135, wherein the unit dosage form is a tablet, wherein the tablet is prepared by a dry granulation process.

Embodiment 139. The method of any one of embodiments 80-138, wherein the unit dosage form is a gastro-resistant tablet.

Embodiment 140. The method of embodiment 139, wherein the gastro-resistant tablet does not substantially disintegrate at a pH at or below 5.5, wherein disintegration is determined by measuring dissolution of the gastro-resistant tablet in a medium having a pH at or below 5.5.

Embodiment 141. The method of embodiment 140, wherein the medium having a pH at or below 5.5 is 0.1N HCl solution having a pH of 1.2.

Embodiment 142. The method of embodiment 139, wherein the gastro-resistant tablet substantially disintegrates at a pH of about 6.8, wherein disintegration is determined by measuring dissolution of the gastro-resistant tablet in a medium having a pH of 6.8.

Embodiment 143. The method of embodiment 142, wherein the medium having a pH of 6.8 is a phosphate buffer.

Embodiment 144. The method of embodiment 139, wherein gastro-resistant tablet does not substantially disintegrate in gastric fluid.

Embodiment 145. The method of embodiment 139, wherein the gastro-resistant tablet substantially disintegrates in intestinal fluid.

Embodiment 146. The method of any one of embodiments 80-145, wherein the subject is in a fed state.

Embodiment 147. The method of any one of embodiments 80-145, wherein the subject is in a fasted state.

Embodiment 148. The method of any one of embodiments 80-147, further comprising administering to the subject a therapeutically-effective amount of a gastric acid-reducing agent.

Embodiment 149. The method of embodiment 148, wherein the gastric acid-reducing agent is administered concurrently with the pharmaceutical composition.

Embodiment 150. The method of embodiment 148, wherein the gastric acid-reducing agent is administered sequentially, before or after the pharmaceutical composition.

Embodiment 151. The method of any one of embodiments 148-150, wherein the gastric acid-reducing agent is a proton-pump inhibitor.

Embodiment 152. The method of any one of embodiments 148-151 wherein the gastric acid-reducing agent is an antacid.

Embodiment 153. The method of any one of embodiments 148-151, wherein the gastric acid-reducing agent is a histamine $H_2$ receptor antagonist.

Embodiment 154. The method of any one of embodiments 80-147, wherein the pharmaceutical composition is administered in absence of a gastric acid-reducing agent.

Embodiment 155. The method of any one of embodiments 80-154, wherein the unit dosage form is a gastro-resistant tablet, wherein the gastro-resistant tablet comprises a core and a coating layer substantially covering the core.

Embodiment 156. The method of embodiment 155, wherein the coating layer comprises an enteric polymer.

Embodiment 157. The method of embodiment 156, wherein the enteric polymer is hypromellose acetate succinate.

Embodiment 158. The method of embodiment 155, wherein the coating layer is about 20% by mass of the tablet.

Embodiment 159. The method of embodiment 155, wherein the gastro-resistant tablet further comprises a sub-coating layer between the core and the coating layer.

Embodiment 160. The method of embodiment 159, wherein the sub-coating layer comprises a polymer.

Embodiment 161. The method of embodiment 160, wherein the polymer is hypromellose.

Embodiment 162. The method of any one of embodiments 159-161, wherein the sub-coating layer is about 3% by mass of the tablet.

Embodiment 163. The method of any one of embodiments 80-162, wherein treatment increases RyR1-Calstabin1 binding in skeletal muscle of the subject.

Embodiment 164. The method of any one of embodiments 80-163, wherein treatment decreases calcium leak from RyR1 channels of the subject.

Embodiment 165. A pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 2 to about 6 hours after administration.

Embodiment 166. The pharmaceutical composition of embodiment 165, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 3 to about 4 hours after administration.

Embodiment 167. The pharmaceutical composition of embodiment 165 or embodiment 166, comprising the pharmaceutically-acceptable salt, wherein the pharmaceutically-acceptable salt is a hemifumarate salt.

Embodiment 168. The pharmaceutical composition of any one of embodiments 165-167, wherein the unit dosage form is a modified release dosage form.

Embodiment 169. The pharmaceutical composition of any one of embodiments 165-168, wherein the unit dosage form is a delayed release dosage form.

Embodiment 170. The pharmaceutical composition of any one of embodiments 165-169, wherein the unit dosage form is suitable for oral administration.

Embodiment 171. The pharmaceutical composition of any one of embodiments 165-170, wherein the unit dosage form is a solid dosage form.

Embodiment 172. The pharmaceutical composition of any one of embodiments 165-171, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 12 hours.

Embodiment 173. The pharmaceutical composition of any one of embodiments 165-171, wherein in a controlled study, if the unit dosage form is administered to a study subject, then a therapeutically-effective amount of 4-[(7-methoxy-2,3-dihydro-1,4-benzothiazepin-4(5H)yl)methyl]benzoic acid or the pharmaceutically-acceptable salt thereof is present in the subject over a period of time, wherein the period of time occurs after administration, wherein the period of time is at least about 24 hours.

Embodiment 174. The pharmaceutical composition of any one of embodiments 165-171, wherein in a controlled study, if the unit dosage form is administered to a study subject, then an in-vivo half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof of about 14 to about 21 hours is obtained in the subject.

Embodiment 175. The pharmaceutical composition of any one of embodiments 165-171, wherein in a controlled study, if the unit dosage form is administered to a study subject, then an accumulation ratio for $C_{max}$ of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio is calculated as a ratio of $C_{max}$ on Day 28/$C_{max}$ on Day 1, wherein $C_{max}$ is maximum observed plasma concentration.

Embodiment 176. The pharmaceutical composition of any one of embodiments 165-171, wherein in a controlled study, if the unit dosage form is administered to a study subject, then an accumulation ratio for AUC of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8 is present in the subject, wherein said accumulation ratio for AUC is calculated as a ratio of $AUC_{tau}$ on Day 28/$AUC_{0-24}$ Day 1, wherein
AUC is area under the concentration-time curve;
$AUC_{tau}$ is area under the concentration-time curve during a dosing interval (tau) at steady-state; and
$AUC_{0-24}$ is area under the concentration-time curve, from time 0 to 24 hours post-dose.

Embodiment 177. The pharmaceutical composition of any one of embodiments 165-171, wherein in a controlled study, if the unit dosage form is administered to a study subject, then a maximum observed plasma concentration of less than about 35 ug/mL of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject.

Embodiment 178. The pharmaceutical composition of any one of embodiments 165-171, wherein in a controlled study, if the unit dosage form is administered to a study subject, then a steady-state plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof occurs in the study subject in a range of about 3 to about 7 days after initial administration.

Embodiment 179. The pharmaceutical composition of any one of embodiments 165-178, comprising 20 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 180. The pharmaceutical composition of any one of embodiments 165-178, comprising 50 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 181. The pharmaceutical composition of any one of embodiments 165-178, comprising 100 mg of 4-[(7-methoxy-2,3-dihydro-1,4-benzothiazepin-4(5H)yl)methyl]benzoic acid hemifumarate, based on mass of 4-[(7-methoxy-2,3-dihydro-1,4-benzothiazepin-4(5H)yl)methyl]benzoic acid.

Embodiment 182. The pharmaceutical composition of any one of embodiments 165-181, wherein the unit dosage form is a gastro-resistant tablet.

Embodiment 183. The pharmaceutical composition of embodiment 182, wherein the gastro-resistant tablet does not substantially disintegrate at a pH at or below 5.5, wherein disintegration is determined by measuring dissolution of the gastro-resistant tablet in a medium having a pH at or below 5.5.

Embodiment 184. The pharmaceutical composition of embodiment 182, wherein the gastro-resistant tablet substantially disintegrates at a pH of at least about 6.8, wherein disintegration is determined by measuring dissolution of the gastro-resistant tablet in a medium having a pH of 6.8.

Embodiment 185. The pharmaceutical composition of any one of embodiments 165-184, wherein the unit dosage form is a gastro-resistant tablet, wherein the gastro-resistant tablet comprises a core and a coating layer substantially covering the core.

Embodiment 186. The pharmaceutical composition of embodiment 185, wherein the coating layer comprises an enteric polymer.

Embodiment 187. The pharmaceutical composition of embodiment 186, wherein the enteric polymer is hypromellose acetate succinate.

Embodiment 188. The pharmaceutical composition of embodiment 185, further comprising a sub-coating layer between the core and the coating layer.

Embodiment 189. The pharmaceutical composition of embodiment 188, wherein the sub-coating layer comprises a polymer.

Embodiment 190. The pharmaceutical composition of embodiment 189, wherein the polymer is hypromellose.

Embodiment 191. A method of treating a condition, comprising administering to a subject in need thereof a therapeutically-effective amount of a pharmaceutical composition, the pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein in a controlled study, if the unit dosage form is administered to a study subject, then a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof is present in the subject at a time between about 2 to about 6 hours after administration.

Embodiment 192. The method of embodiment 191, wherein the condition is catecholaminergic polymorphic ventricular tachycardia.

Embodiment 193. The method of embodiment 191, wherein the condition is RYR1-related myopathy.

Embodiment 194. A tablet comprising a core, a sub-coating layer substantially covering the core, and a coating layer substantially covering the sub-coating layer, wherein
the core comprises 4-[(7-methoxy-2,3-dihydro-1,4-benzothiazepin-4(5H)yl)methyl]benzoic acid hemifumarate, mannitol, microcrystalline cellulose, croscarmellose sodium, magnesium stearate, maltodextrin, colloidal anhydrous silica, and sodium stearyl fumarate;
the sub-coating layer comprises hypromellose, microcrystalline cellulose and stearic acid; and
the coating layer comprises hypromellose acetate succinate, triethyl citrate, sodium lauryl sulfate, and talc.

Embodiment 195. A tablet comprising a core, a sub-coating layer substantially covering the core, and a coating layer substantially covering the sub-coating layer, wherein
the core comprises 20 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
the sub-coating layer comprises hypromellose, microcrystalline cellulose, and stearic acid; and
the coating layer comprises hypromellose acetate succinate, triethyl citrate, sodium lauryl sulfate, and talc.
Embodiment 196. A tablet comprising a core, a sub-coating layer substantially covering the core, and a coating layer substantially covering the sub-coating layer, wherein
the core comprises 50 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
the sub-coating layer comprises hypromellose, microcrystalline cellulose, and stearic acid; and
the coating layer comprises hypromellose acetate succinate, triethyl citrate, sodium lauryl sulfate, and talc.
Embodiment 197. A tablet comprising a core, a sub-coating layer substantially covering the core, and a coating layer substantially covering the sub-coating layer, wherein
the core comprises 100 mg of 4-[(7-methoxy-2,3-dihydro-1,4-benzothiazepin-4(5H)yl)methyl]benzoic acid hemifumarate based on the mass of 4-[(7-methoxy-2,3-dihydro-1,4-benzothiazepin-4(5H)yl)methyl]benzoic acid, mannitol, microcrystalline cellulose, croscarmellose sodium, magnesium stearate, maltodextrin, colloidal anhydrous silica, and sodium stearyl fumarate;
the sub-coating layer comprises hypromellose, microcrystalline cellulose, and stearic acid; and
the coating layer comprises hypromellose acetate succinate, triethyl citrate, sodium lauryl sulfate, and talc.
Embodiment 198. A tablet comprising:

| | Component | Ratio (%) |
|---|---|---|
| Core | 4-[(7-methoxy-2,3-dihydro-1,4-benzothiazepin-4(5H)yl)methyl]benzoic acid hemifumarate | 38.18 |
| | Mannitol | 11.01 |
| | Cellulose, microcrystalline | 16.23 |
| | Croscarmellose sodium | 2.44 |
| | Magnesium stearate | 0.81 |
| | Maltodextrin | 11.53 |
| | Silica, colloidal anhydrous | 0.16 |
| | Sodium stearyl fumarate | 0.81 |
| Sub-coating | Colourless Sepifilm LP 010: | |
| | Hypromellose | 1.94 |
| | Cellulose, microcrystalline | 0.24 |
| | Stearic acid | 0.24 |
| | Purified water | q.s. |
| Enteric Coating | AQOAT suspension: | |
| | Hypromellose acetate succinate | 10.18 |
| | Triethyl citrate | 2.85 |
| | Sodium laurilsulfate | 0.31 |
| | Talc | 3.06 |
| | Purified water | q.s. |

What is claimed is:

1. A method of treating catecholaminergic polymorphic ventricular tachycardia, comprising administering to a subject in need thereof a therapeutically-effective amount of a pharmaceutical composition, the pharmaceutical composition comprising in a unit dosage form 4-[(7-methoxy-2,3-dihydro-1,4-benzothiazepin-4(5H)yl)methyl]benzoic acid or a pharmaceutically-acceptable salt thereof, and a pharmaceutically-acceptable excipient, wherein when administered to a subject, the pharmaceutical composition provides to the subject a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof at a time between about 2 to about 6 hours after administration.

2. The method of claim 1, wherein when administered to the subject, the pharmaceutical composition provides to the subject a maximum plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof at a time between about 3 to about 4 hours after administration.

3. The method of claim 1, wherein the pharmaceutical composition comprises the pharmaceutically-acceptable salt, wherein the pharmaceutically-acceptable salt is a hemifumarate salt.

4. The method of claim 1, wherein the unit dosage form is a modified release dosage form.

5. The method of claim 1, wherein the unit dosage form is a delayed release dosage form.

6. The method of claim 1, wherein when administered to the subject, the pharmaceutical composition provides to the subject an in-vivo mean terminal half-life of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof of about 14 to about 21 hours after administration.

7. The method of claim 1, wherein when administered to the subject, the pharmaceutical composition provides to the subject an accumulation ratio for $C_{max}$ of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8, wherein said accumulation ratio is calculated as a ratio of $C_{max}$ on Day 28/$C_{max}$ on Day 1, wherein $C_{max}$ is maximum observed plasma concentration.

8. The method of claim 1, wherein when administered to the subject, the pharmaceutical composition provides to the subject an accumulation ratio for AUC of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof between about 1.4 and about 1.8, wherein said accumulation ratio for AUC is calculated as a ratio of $AUC_{tau}$ on Day 28/$AUC_{0-24}$ Day 1, wherein AUC is area under the concentration-time curve;
$AUC_{tau}$ is area under the concentration-time curve during a dosing interval (tau) at steady-state; and
$AUC_{0-24}$ is area under the concentration-time curve, from time 0 to 24 hours post-dose.

9. The method of claim 1, wherein when administered to the subject, the pharmaceutical composition provides to the subject a steady-state plasma concentration of 4-[(7-methoxy-2,3-dihydro-1,4-benzothiazepin-4(5H)yl)methyl]benzoic acid or the pharmaceutically-acceptable salt thereof or a pharmaceutically-acceptable ion thereof in a range of about 3 to about 7 days after initial administration.

10. The method of claim 1, wherein the unit dosage form is suitable for oral administration.

11. The method of claim 1, wherein the unit dosage form is a gastro-resistant tablet.

12. The method of claim 1, wherein the catecholaminergic polymorphic ventricular tachycardia is catecholaminergic polymorphic ventricular tachycardia type 1.

* * * * *